United States Patent
Stroncek et al.

(10) Patent No.: US 9,808,298 B2
(45) Date of Patent: Nov. 7, 2017

(54) OPEN-ARCHITECTURE INTERFERENCE SCREW

(71) Applicant: Smith & Nephew, Inc., Memphis, TN (US)

(72) Inventors: John Stroncek, Boston, MA (US); Alfred R. Berube, Jr., North Attelboro, MA (US); Kirsten H. Aarsvold, Mansfield, MA (US)

(73) Assignee: Smith & Nephew, Inc., Memphis, TN (US)

( * ) Notice: Subject to any disclaimer, the term of this patent is extended or adjusted under 35 U.S.C. 154(b) by 389 days.

(21) Appl. No.: 14/249,020

(22) Filed: Apr. 9, 2014

(65) Prior Publication Data

US 2014/0303676 A1    Oct. 9, 2014

Related U.S. Application Data

(60) Provisional application No. 61/810,007, filed on Apr. 9, 2013.

(51) Int. Cl.
| | |
|---|---|
| *A61B 17/86* | (2006.01) |
| *A61B 17/88* | (2006.01) |
| *A61F 2/08* | (2006.01) |

(52) U.S. Cl.
CPC .......... *A61B 17/864* (2013.01); *A61B 17/869* (2013.01); *A61B 17/8635* (2013.01);
(Continued)

(58) Field of Classification Search
CPC ....... A61B 17/86; A61B 17/88; A61B 17/864; A61B 17/8645; A61B 17/8875
(Continued)

(56) References Cited

U.S. PATENT DOCUMENTS

| | | |
|---|---|---|
| 2,288,864 A | 7/1942 | Whitehead et al. |
| 3,316,795 A | 5/1967 | David |

(Continued)

FOREIGN PATENT DOCUMENTS

| | | |
|---|---|---|
| CN | 2732211 | 10/2005 |
| CN | 1701772 A | 11/2005 |

(Continued)

OTHER PUBLICATIONS

First Office Action for Chinese Patent Application No. 201180013194.3, dated Jul. 21, 2014.
(Continued)

*Primary Examiner* — Christopher Beccia
(74) *Attorney, Agent, or Firm* — Burns & Levinson LLP; Joseph M. Maraia

(57) ABSTRACT

The present disclosure relates to an interference screw for creating an interference fit between a bone tunnel and tissue. The screw includes a threaded body having a proximal end, distal end, and thread extending around the threaded body between the proximal and distal ends. A supporting spline extends along a cannulation through the threaded body. The supporting spline is engagable with a delivery device. The screw further includes at least one opening defined by a surface between threads of the threaded body. A ratio of open surface area to closed surface area defines the opening and is selected such that, when torsionally loaded, the screw does not exhibit plastic deformation when inserted into an undersized bone tunnel. The screw further includes a tapered tip extending from the distal end of the threaded body. The tapered tip has a thread extending at least partway around the tapered tip.

22 Claims, 30 Drawing Sheets

(52) U.S. Cl.
CPC ........ *A61B 17/8645* (2013.01); *A61B 17/888* (2013.01); *A61F 2/0811* (2013.01); *A61F 2002/0817* (2013.01); *A61F 2002/0841* (2013.01)

(58) Field of Classification Search
USPC .................................................. 600/300–331
See application file for complete search history.

(56) References Cited

U.S. PATENT DOCUMENTS

| | | |
|---|---|---|
| 3,320,783 A | 5/1967 | Kerr |
| 3,499,222 A | 3/1970 | Linkow et al. |
| 3,716,058 A | 2/1973 | Tanner |
| 3,821,975 A | 7/1974 | Haker |
| 3,869,942 A | 3/1975 | DeCaro |
| 3,874,258 A | 4/1975 | Semola et al. |
| 4,027,572 A | 6/1977 | Burge |
| 4,177,797 A | 12/1979 | Baylis et al. |
| D288,777 S | 3/1987 | Kwon |
| 4,653,489 A | 3/1987 | Tronzo |
| 4,738,255 A | 4/1988 | Goble et al. |
| 4,741,651 A | 5/1988 | Despres |
| 4,834,757 A | 5/1989 | Brantigan |
| 4,854,311 A | 8/1989 | Steffee |
| RE33,114 E | 11/1989 | Chiavon |
| 4,913,143 A | 4/1990 | Oloff et al. |
| 4,961,740 A | 10/1990 | Ray et al. |
| 4,988,351 A | 1/1991 | Paulos et al. |
| 5,026,373 A | 6/1991 | Ray et al. |
| 5,055,104 A | 10/1991 | Ray |
| 5,094,133 A | 3/1992 | Schreiber |
| 5,116,337 A | 5/1992 | Johnson |
| 5,129,904 A | 7/1992 | Illi |
| 5,129,906 A | 7/1992 | Ross et al. |
| 5,139,520 A | 8/1992 | Rosenberg |
| 5,197,967 A | 3/1993 | Wilson |
| 5,236,431 A | 8/1993 | Gogolewski et al. |
| 5,242,447 A | 9/1993 | Borzone |
| 5,312,214 A | 5/1994 | Morton |
| 5,354,299 A | 10/1994 | Coleman |
| 5,364,400 A | 11/1994 | Rego, Jr. et al. |
| 5,370,662 A | 12/1994 | Stone et al. |
| 5,383,878 A | 1/1995 | Roger et al. |
| 5,407,427 A | 4/1995 | Zhu et al. |
| 5,411,506 A | 5/1995 | Goble et al. |
| 5,411,523 A | 5/1995 | Goble |
| 5,423,823 A | 6/1995 | Schmieding |
| 5,431,660 A | 7/1995 | Burke |
| 5,447,533 A | 9/1995 | Vachon et al. |
| 5,464,427 A | 11/1995 | Curtis et al. |
| 5,470,334 A | 11/1995 | Ross et al. |
| 5,531,780 A | 7/1996 | Vachon |
| 5,571,139 A | 11/1996 | Jenkins, Jr. |
| 5,573,548 A | 11/1996 | Nazre et al. |
| 5,593,409 A | 1/1997 | Michelson |
| 5,609,635 A | 3/1997 | Michelson |
| 5,609,636 A | 3/1997 | Kohrs et al. |
| 5,626,613 A | 5/1997 | Schmieding |
| 5,632,747 A | 5/1997 | Scarborough |
| 5,645,547 A | 7/1997 | Coleman |
| 5,658,285 A | 8/1997 | Marnay et al. |
| 5,676,545 A | 10/1997 | Jones |
| 5,681,352 A | 10/1997 | Clancy, III et al. |
| 5,688,285 A | 11/1997 | Yamada |
| 5,690,676 A | 11/1997 | Dipoto et al. |
| 5,695,497 A | 12/1997 | Stahelin |
| 5,702,397 A | 12/1997 | Goble et al. |
| 5,709,683 A | 1/1998 | Bagby |
| 5,802,794 A | 9/1998 | Robson |
| 5,833,715 A | 11/1998 | Vachon et al. |
| 5,876,405 A | 3/1999 | Del Rio |
| 5,888,227 A | 3/1999 | Cottle |
| 5,891,146 A | 4/1999 | Simon et al. |
| 5,921,982 A | 7/1999 | Lesh et al. |
| 5,951,560 A | 9/1999 | Simon et al. |
| 5,961,524 A | 10/1999 | Crombie |
| 5,964,783 A | 10/1999 | Grafton et al. |
| 5,968,047 A | 10/1999 | Reed |
| 5,968,098 A | 10/1999 | Winslow |
| 5,984,967 A | 11/1999 | Zdeblick et al. |
| 6,008,433 A | 12/1999 | Stone |
| 6,039,762 A | 3/2000 | McKay |
| 6,086,593 A | 7/2000 | Bonutti |
| 6,096,060 A | 8/2000 | Fitts et al. |
| 6,097,986 A | 8/2000 | Janke et al. |
| 6,132,435 A | 10/2000 | Young |
| 6,146,073 A | 11/2000 | Kobusch |
| 6,196,780 B1 | 3/2001 | Wakai et al. |
| 6,214,031 B1 | 4/2001 | Schmieding et al. |
| 6,235,057 B1 | 5/2001 | Roger et al. |
| 6,283,973 B1 | 9/2001 | Hubbard et al. |
| 6,302,632 B1 | 10/2001 | Lin |
| 6,360,129 B1 | 3/2002 | Ley et al. |
| 6,443,989 B1 | 9/2002 | Jackson |
| 6,447,545 B1 | 9/2002 | Bagby |
| 6,488,683 B2 | 12/2002 | Lieberman |
| 6,503,251 B1 | 1/2003 | Shadduck |
| 6,511,499 B2 | 1/2003 | Schmieding et al. |
| 6,514,257 B2 | 2/2003 | Dovesi et al. |
| 6,517,542 B1 | 2/2003 | Papay et al. |
| 6,527,774 B2 | 3/2003 | Lieberman |
| 6,544,265 B2 | 4/2003 | Lieberman |
| 6,551,319 B2 | 4/2003 | Lieberman |
| 6,551,320 B2 | 4/2003 | Lieberman |
| 6,551,322 B1 | 4/2003 | Lieberman |
| 6,554,830 B1 | 4/2003 | Chappius |
| 6,569,188 B2 | 5/2003 | Grafton et al. |
| 6,589,245 B1 | 7/2003 | Weiler et al. |
| 6,604,945 B1 | 8/2003 | Jones |
| 6,626,917 B1 | 9/2003 | Craig |
| 6,648,903 B1 | 11/2003 | Pierson |
| 6,656,183 B2 | 12/2003 | Colleran et al. |
| 6,666,888 B1 | 12/2003 | Jackson |
| 6,685,728 B2 | 2/2004 | Sinnott et al. |
| 6,818,010 B2 | 11/2004 | Eichhorn et al. |
| 6,823,871 B2 | 11/2004 | Schmieding |
| 6,855,168 B2 | 2/2005 | Crozet |
| 6,857,343 B1 | 2/2005 | Easterbrooks |
| 6,863,671 B1 * | 3/2005 | Strobel ................. A61F 2/0811 606/314 |
| 6,942,669 B2 | 9/2005 | Kurc |
| 6,953,462 B2 | 10/2005 | Lieberman |
| 7,033,372 B1 | 4/2006 | Cahalan |
| 7,070,586 B2 | 7/2006 | Hart et al. |
| 7,083,647 B1 | 8/2006 | Sklar et al. |
| 7,090,690 B2 | 8/2006 | Foerster et al. |
| 7,147,641 B2 | 12/2006 | Chen |
| 7,189,251 B2 * | 3/2007 | Kay ................... A61B 17/0401 411/395 |
| 7,195,634 B2 | 3/2007 | Schmieding et al. |
| 7,217,279 B2 | 5/2007 | Reese |
| 7,322,978 B2 | 1/2008 | West |
| 7,322,986 B2 | 1/2008 | Wolf |
| 7,335,221 B2 | 2/2008 | Collier et al. |
| 7,371,244 B2 | 5/2008 | Chatlynne et al. |
| 7,572,264 B2 | 8/2009 | Null et al. |
| 7,575,572 B2 | 8/2009 | Sweeney |
| 7,585,311 B2 | 9/2009 | Green et al. |
| 7,594,929 B2 | 9/2009 | Collette |
| 7,608,098 B1 | 10/2009 | Stone et al. |
| 7,867,252 B2 | 1/2011 | Criscuolo et al. |
| 7,883,529 B2 | 2/2011 | Sinnott et al. |
| 7,896,902 B2 | 3/2011 | Jeon et al. |
| 7,914,539 B2 | 3/2011 | Stone et al. |
| 7,935,138 B1 | 5/2011 | Richelsoph |
| 7,993,369 B2 | 8/2011 | Dreyfuss |
| 8,016,865 B2 | 9/2011 | Donnelly et al. |
| 8,034,090 B2 | 10/2011 | Stone et al. |
| 8,167,906 B2 | 5/2012 | Cauldwell et al. |
| 8,343,186 B2 | 1/2013 | Dreyfuss et al. |
| 8,372,124 B2 | 2/2013 | Paulk et al. |
| 8,430,909 B2 | 4/2013 | Dreyfuss |
| 8,449,613 B2 | 5/2013 | Crozet |

(56) References Cited

U.S. PATENT DOCUMENTS

| | | |
|---|---|---|
| 8,480,686 B2 | 7/2013 | Bakos |
| 8,597,328 B2 | 12/2013 | Cauldwell et al. |
| 8,623,049 B2 | 1/2014 | Ward |
| 8,623,052 B2 | 1/2014 | Dreyfuss et al. |
| 8,636,799 B2 | 1/2014 | Sklar et al. |
| 8,672,967 B2 | 3/2014 | Dimatteo et al. |
| 8,715,282 B2 | 5/2014 | Pool |
| 8,801,755 B2 | 8/2014 | Dreyfuss et al. |
| 8,821,541 B2 | 9/2014 | Dreyfuss et al. |
| 8,974,505 B2 | 3/2015 | Sawa et al. |
| 8,979,848 B2 | 3/2015 | Butters et al. |
| 8,979,865 B2 | 3/2015 | Fan et al. |
| 9,155,531 B2 | 10/2015 | Housman |
| 9,162,350 B2 | 10/2015 | Nino et al. |
| 9,237,887 B2 | 1/2016 | Wack et al. |
| 9,308,080 B2 | 4/2016 | Housman et al. |
| 9,393,006 B2 | 7/2016 | Housman et al. |
| 9,427,270 B2 | 8/2016 | Housman |
| 9,526,488 B2 | 12/2016 | Arai et al. |
| 9,579,188 B2 | 2/2017 | Bowman et al. |
| 2002/0022862 A1 | 2/2002 | Grafton et al. |
| 2002/0052629 A1 | 5/2002 | Morgan et al. |
| 2002/0055737 A1 | 5/2002 | Lieberman |
| 2002/0055738 A1 | 5/2002 | Lieberman |
| 2002/0055742 A1 | 5/2002 | Lieberman |
| 2002/0087189 A1 | 7/2002 | Bonutti |
| 2002/0087190 A1 | 7/2002 | Benavitz et al. |
| 2002/0099382 A1 | 7/2002 | Salazar et al. |
| 2002/0111653 A1 | 8/2002 | Foerster |
| 2002/0143335 A1 | 10/2002 | von Hoffmann et al. |
| 2002/0165546 A1 | 11/2002 | Goble et al. |
| 2003/0055431 A1 | 3/2003 | Brannon |
| 2003/0065361 A1 | 4/2003 | Dreyfuss |
| 2003/0065374 A1 | 4/2003 | Honeck |
| 2003/0069640 A1 | 4/2003 | Ferreira et al. |
| 2003/0078585 A1 | 4/2003 | Johnson et al. |
| 2003/0125749 A1 | 7/2003 | Yuan et al. |
| 2003/0181913 A1 | 9/2003 | Lieberman |
| 2003/0195529 A1 | 10/2003 | Takamoto et al. |
| 2004/0015170 A1 | 1/2004 | Tallarida et al. |
| 2004/0030343 A1 | 2/2004 | Kurc |
| 2004/0039404 A1 | 2/2004 | Dreyfuss |
| 2004/0073216 A1 | 4/2004 | Lieberman |
| 2004/0093032 A1 | 5/2004 | Sinnott et al. |
| 2004/0097945 A1 | 5/2004 | Wolf |
| 2004/0122424 A1 | 6/2004 | Ferree |
| 2004/0143158 A1 | 7/2004 | Hart et al. |
| 2004/0143237 A1 | 7/2004 | Hart et al. |
| 2004/0153074 A1 | 8/2004 | Bojarski et al. |
| 2004/0267265 A1 | 12/2004 | Kyle |
| 2005/0107828 A1 | 5/2005 | Reese |
| 2005/0159727 A1 | 7/2005 | Lesh |
| 2005/0222681 A1 | 10/2005 | Richley et al. |
| 2005/0234458 A1 | 10/2005 | Huebner |
| 2005/0250984 A1 | 11/2005 | Lam et al. |
| 2005/0250985 A1 | 11/2005 | Saadat et al. |
| 2005/0250987 A1 | 11/2005 | Ewers et al. |
| 2005/0250988 A1 | 11/2005 | Ewers et al. |
| 2005/0267478 A1 | 12/2005 | Corradi et al. |
| 2005/0283239 A1 | 12/2005 | Crozet |
| 2006/0009769 A1 | 1/2006 | Lieberman |
| 2006/0030948 A1 | 2/2006 | Manrique et al. |
| 2006/0079895 A1 | 4/2006 | McLeer |
| 2006/0079903 A1 | 4/2006 | Wong |
| 2006/0089651 A1 | 4/2006 | Trudeau et al. |
| 2006/0100627 A1 | 5/2006 | Stone et al. |
| 2006/0106390 A1 | 5/2006 | Jensen et al. |
| 2006/0142769 A1 | 6/2006 | Collette |
| 2006/0149266 A1 | 7/2006 | Cordasco |
| 2006/0217681 A1 | 9/2006 | Hart et al. |
| 2006/0241636 A1 | 10/2006 | Novak et al. |
| 2006/0247642 A1* | 11/2006 | Stone ............... A61B 17/8605 623/13.14 |
| 2006/0253080 A1 | 11/2006 | Tulleken et al. |
| 2006/0276841 A1 | 12/2006 | Barbieri et al. |
| 2007/0032797 A1 | 2/2007 | Ortiz et al. |
| 2007/0093895 A1 | 4/2007 | Donnelly et al. |
| 2007/0122764 A1 | 5/2007 | Balfour et al. |
| 2007/0142849 A1 | 6/2007 | Ewers et al. |
| 2007/0185532 A1 | 8/2007 | Stone et al. |
| 2007/0198019 A1 | 8/2007 | Schomer et al. |
| 2007/0203498 A1 | 8/2007 | Gerber et al. |
| 2008/0027446 A1 | 1/2008 | Stone et al. |
| 2008/0065114 A1 | 3/2008 | Stone et al. |
| 2008/0082128 A1 | 4/2008 | Stone |
| 2008/0132932 A1 | 6/2008 | Hoeppner |
| 2008/0140092 A1 | 6/2008 | Stone et al. |
| 2008/0140093 A1 | 6/2008 | Stone et al. |
| 2008/0154314 A1 | 6/2008 | McDevitt |
| 2008/0179839 A1 | 7/2008 | Walters |
| 2008/0275431 A1 | 11/2008 | Stone et al. |
| 2009/0024174 A1 | 1/2009 | Stark |
| 2009/0042951 A1 | 2/2009 | Danziger |
| 2009/0076544 A1 | 3/2009 | DiMatteo et al. |
| 2009/0118776 A1 | 5/2009 | Kelsch et al. |
| 2009/0125071 A1 | 5/2009 | Skinlo et al. |
| 2009/0187216 A1 | 7/2009 | Schmieding et al. |
| 2009/0248029 A1 | 10/2009 | Paulos |
| 2009/0292321 A1 | 11/2009 | Collette |
| 2009/0319043 A1 | 12/2009 | McDevitt et al. |
| 2010/0094297 A1 | 4/2010 | Parmigiani |
| 2010/0094352 A1 | 4/2010 | Iott et al. |
| 2010/0106166 A1 | 4/2010 | Cropper et al. |
| 2010/0274298 A1 | 10/2010 | Schiff |
| 2011/0054526 A1 | 3/2011 | Stone et al. |
| 2011/0112576 A1 | 5/2011 | Nguyen et al. |
| 2011/0130760 A1 | 6/2011 | Anderson et al. |
| 2011/0213426 A1 | 9/2011 | Yedlicka et al. |
| 2011/0224727 A1 | 9/2011 | Housman et al. |
| 2011/0282450 A1 | 11/2011 | Donnelly et al. |
| 2011/0319933 A1 | 12/2011 | Tepic |
| 2012/0041448 A1 | 2/2012 | Schumacher et al. |
| 2012/0059384 A1* | 3/2012 | Fan ............... A61F 2/0805 606/104 |
| 2012/0179163 A1 | 7/2012 | Housman et al. |
| 2012/0330420 A1 | 12/2012 | Brodke et al. |
| 2013/0150859 A1 | 6/2013 | Kehres et al. |
| 2013/0158596 A1 | 6/2013 | Miller et al. |
| 2013/0158597 A1 | 6/2013 | Hernandez |
| 2013/0158598 A1 | 6/2013 | Lizardi |
| 2013/0158599 A1 | 6/2013 | Hester et al. |
| 2013/0158610 A1 | 6/2013 | Hernandez |
| 2013/0178901 A1 | 7/2013 | Arai et al. |
| 2014/0081339 A1 | 3/2014 | Bowman et al. |
| 2014/0142697 A1 | 5/2014 | Sklar et al. |
| 2014/0148850 A1 | 5/2014 | Dimatteo et al. |
| 2014/0172016 A1 | 6/2014 | Housman |
| 2014/0277129 A1 | 9/2014 | Arai et al. |
| 2014/0277130 A1* | 9/2014 | Housman ............... A61B 17/0401 606/232 |
| 2014/0277188 A1 | 9/2014 | Poulos |
| 2014/0277192 A1 | 9/2014 | Housman |
| 2015/0196388 A1 | 7/2015 | Housman et al. |
| 2015/0327984 A1 | 11/2015 | Arai et al. |
| 2016/0235399 A1 | 8/2016 | Housman et al. |
| 2016/0374661 A1 | 12/2016 | Housman et al. |
| 2017/0014224 A1 | 1/2017 | Arai et al. |
| 2017/0020589 A1 | 1/2017 | Bowman et al. |
| 2017/0049438 A1 | 2/2017 | Arai et al. |

FOREIGN PATENT DOCUMENTS

| | | |
|---|---|---|
| CN | 1829479 A | 9/2006 |
| CN | 101002703 | 7/2007 |
| CN | 101031248 A | 9/2007 |
| CN | 101422381 | 5/2009 |
| CN | 101422381 A | 5/2009 |
| CN | 101573078 A | 11/2009 |
| CN | 201436022 U | 4/2010 |
| CN | 102068305 A | 5/2011 |
| CN | 102475586 | 5/2012 |
| CN | 102512253 A | 6/2012 |
| CN | 102525583 A | 7/2012 |
| CN | 102551821 A | 7/2012 |

(56) References Cited

FOREIGN PATENT DOCUMENTS

| | | |
|---|---|---|
| CN | 102781370 | 11/2012 |
| CN | 102905636 A | 1/2013 |
| CN | 102573662 B | 8/2015 |
| EP | 3502698 | 9/1992 |
| EP | 05202698 A1 | 9/1992 |
| EP | 0538895 A2 | 4/1993 |
| EP | 0682917 B1 | 11/1995 |
| EP | 0686373 A1 | 12/1995 |
| EP | 0669110 B1 | 5/2000 |
| EP | 1147751 B1 | 10/2001 |
| EP | 1093774 B1 | 6/2002 |
| EP | 1234637 A2 | 8/2002 |
| EP | 0796593 B1 | 5/2004 |
| EP | 1430843 A2 | 6/2004 |
| EP | 1917926 A1 | 7/2008 |
| EP | 2036501 A3 | 9/2010 |
| EP | 2422711 A2 | 2/2012 |
| EP | 2422712 A1 | 2/2012 |
| EP | 2596758 A1 | 5/2013 |
| EP | 2601894 A1 | 6/2013 |
| FR | 2760355 A1 | 9/1998 |
| FR | 2803739 A1 | 7/2001 |
| FR | 2846867 A1 | 5/2004 |
| FR | 2879915 | 6/2006 |
| FR | 2879915 A1 | 6/2006 |
| GB | 2294399 A | 5/1996 |
| JP | H10-000200 | 1/1998 |
| JP | H10200 A | 1/1998 |
| JP | 2005-529650 | 10/2005 |
| JP | 2006-212449 A | 8/2006 |
| JP | 2006-305348 A | 11/2006 |
| WO | 9608205 A1 | 3/1996 |
| WO | 1996-19947 | 7/1996 |
| WO | 9619947 A1 | 7/1996 |
| WO | 1998-02117 | 1/1998 |
| WO | 9802117 A1 | 1/1998 |
| WO | 9826717 A1 | 6/1998 |
| WO | 2003-063713 | 8/2003 |
| WO | 03063713 A1 | 8/2003 |
| WO | 03/103507 | 12/2003 |
| WO | 03103507 A2 | 12/2003 |
| WO | 2006055516 A2 | 5/2006 |
| WO | 2007093192 A1 | 8/2007 |
| WO | 2008-021474 | 2/2008 |
| WO | 2008021474 A2 | 2/2008 |
| WO | 2008100944 A1 | 8/2008 |
| WO | 2009-042951 | 4/2009 |
| WO | 2009042951 A1 | 4/2009 |
| WO | 2010009217 A1 | 1/2010 |
| WO | 2010017631 A1 | 2/2010 |
| WO | 20100017584 | 2/2010 |
| WO | 2010053708 A1 | 5/2010 |
| WO | 2011059995 A2 | 5/2011 |
| WO | 2011060022 A2 | 5/2011 |
| WO | 2011112776 A1 | 9/2011 |
| WO | 20110112576 | 9/2011 |
| WO | 20120129388 | 9/2012 |
| WO | 2012171011 A1 | 12/2012 |

OTHER PUBLICATIONS

International Search and Written Opinion for PCT/US2014/022539 dated Jun. 27, 2014.
International Search and Written Opinion for PCT/US2014/020747 dated Jun. 6, 2014.
Decision of Rejections for Japanese Patent Application No. 2011-538642, dated Jun. 2, 2014.
International Search and Written Opinion for PCT/US2014/066389 dated Feb. 17, 2015.
Notice of Reasons for Rejection for Japanese Patent Application No. 2012-557236 dated Mar. 2, 2015.
Patent Examination Report No. 1 for Australian Patent Application No. 2011224326 dated Apr. 21, 2015.
Second Office Action for Chinese Patent Application No. 201180013194.3, dated Mar. 23, 2015.
First Office Action for Chinese Patent Application No. 201280022627.6, dated Apr. 13, 2015.
Second Office Action for related Chinese Patent Application No. 201280022627.6 dated Sep. 16, 2015.
Substantive Examination for related Mexican Patent Application No. Mx/a/2013/010383 issued Aug. 12, 2015.
Patent Examination Report No. 1 for related Australian Patent Application No. 2012229152 Issued Aug. 18, 2015.
Third Office Action for related Chinese Patent Application No. 2011-80013194.3 issued Aug. 21, 2015.
International Preliminary Report on Patentability for related International Application No. PCT/US2014/033535, dated Oct. 22, 2015.
Decision of Rejection on related Japanese Patent Application No. 2012-557236 dated Oct. 9, 2015.
Communication from related European Patent Application No. 09761114.9 dated Dec. 3, 2015.
Communication from related European Patent Application No. 11710940.5 dated Dec. 8, 2015.
First Office Action for related Chinese Patent Application No. 201280038677.3 dated Sep. 6, 2015.
Patent Examination Report No. 1 for related Australian Patent Application No. 2012267924 dated Dec. 22, 2015.
Substantive Examination Report from related Mexico Patent Application No. MX/a/2013/010383 dated Jan. 19, 2016.
Notice of Reasons for Rejection for related Japanese Application No. 2013-558094 dated Feb. 2, 2016.
Substantive Examination of related Russian Application No. 2013144961/14(069526) dated Dec. 23, 2015.
Third Office Action from related Chines Application No. 201280022627.6 dated Mar. 4, 2016.
Second Office Action from related Chinese Application No. 201280038677.3 dated May 5, 2016.
International Preliminary Report on Patentability from related PCT Application No. PCT/US2014/066389 dated May 24, 2016.
Office Action from related Mexican Application No. MX/a/2013/010383 dated May 3, 2016.
Notice of Reasons for Rejection from related Japanese Application No. 2014-514625 dated Jun. 13, 2016.
Communication from EPO from related European Application No. 12711719.0-1666 dated Jul. 28, 2016.
Office Action from related Russian Application No. 2015147534/20(073143) dated Jun. 29, 2016.
Hunt, Patrick, D.V.M. et al. "Development of a Perforated Biodegradable Interference Screw", Arthroscopy: The Journal of Arthroscopic and Related Surgery, vol. 21, No. 3, Mar. 2005; pp. 258-265.
International Search and Written Opinion for PCT/US2011/027837 dated May 19, 2011.
Smith & Nephew brochure titled "Bio RCI™ Bioabsorbable Screws: Anatomically Targeted Screws for ACL and PCL Reconstruction", 2000.
Biomet brochure "Bio-Core™ Interference Screw", 2007.
International Search and Written Opinion for PCT/US2009/065304 dated Jun. 5, 2013.
International Search and Written Opinion for PCT/US2012/041298 dated Jun. 5, 2013.
International Search and Written Opinion for PCT/US2012/028803 dated Oct. 24, 2010.
Notice of Reasons for Rejections for Japanese Patent Application No. 2011-538642, dated Oct. 1, 2013.
First Office Action for Chinese Patent Application No. 200980155954.7, dated Apr. 12, 2013.
Second Office Action for Chinese Patent Application No. 200980155954.7, dated Oct. 24, 2013.
Notice of Reasons for Rejection for Japanese Patent Application No. 2012-557236 dated Nov. 25, 2014.
Patent Examination Report No. 1 for Australian Patent Application No. 2009319879 dated Nov. 10, 2014.
Office Action and Search Report from related Chinese Application No. 201480032876.2 dated Oct. 19, 2016.

(56) References Cited

OTHER PUBLICATIONS

Office Communication from related European Application No. 14712930.8-1662 dated Nov. 24, 2016.
Decision of Rejection from related Japanese Application No. 2013-558094 dated Sep. 5, 2016.
First Office Action from related Chinese Application No. 201480012203.0 dated Aug. 17, 2016.
Third Office Action from related Chinese Application No. 201280038677.3 dated Nov. 28, 2016.
Office Action from related Japanese Application No. 2014-514625 dated Dec. 19, 2016.
Office Action from related Russian Application No. 2016124173/20(037886) dated Jan. 19, 2017.
Office Action from related EPO Application No. 14716107.9-1664 dated Mar. 23, 2017.
Communication from related European Application No. 14724272.1-1664 issued Jun. 13, 2017.
First Office Action for Chinese Patent Application No. 201480073698.8 issued May 2, 2017.
First Office Action from related Chinese Application No. 201480014353.5 issued Apr. 19, 2017.
Fourth Office Action from related Chinese Application No. 201280038677.3 issued May 26, 2017.
International Search and Written Opinion for PCT/US2014/033535 dated Jul. 18, 2014.
Office Action from related Russian Application No. 2015147534/20(073143) issued Jun. 29, 2016.
Second Office Action for Chinese Patent Application No.: 201180013194.3, issued Mar. 23, 2015.
Second Office Action from related Chinese Application No. 201480012203.0 issued Apr. 24, 2017.
Second Office Action from related Chinese Application No. 201480032876.2 issued May 31, 2017.

\* cited by examiner

Healicoil screw driver having grooves to allow the screw to insert into the drive until reaching a distal stop.

Shows example driver 150 used to insert the interference screw 100 into a bone tunnel.

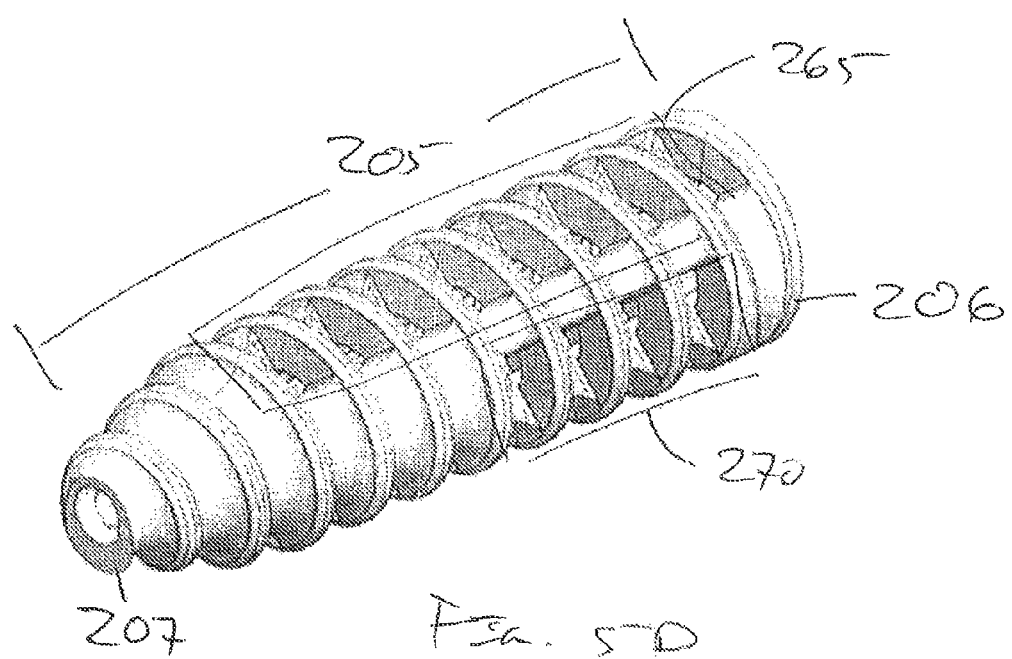

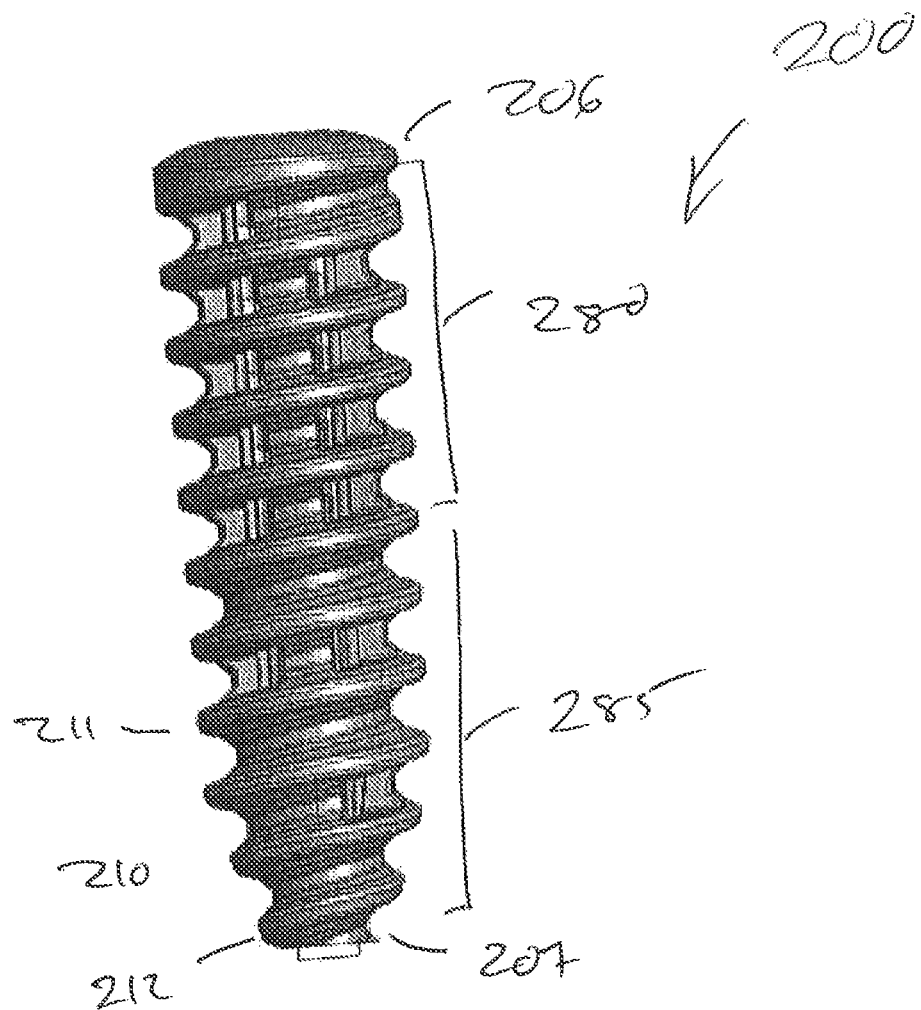

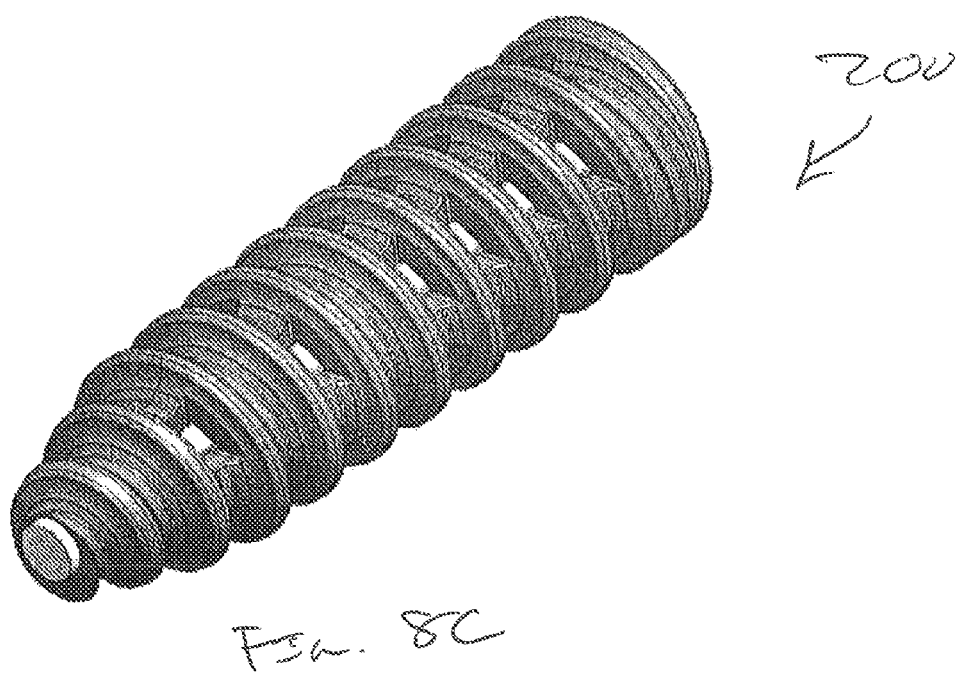

Example driver extending through entire screw length and fully supporting the screw.

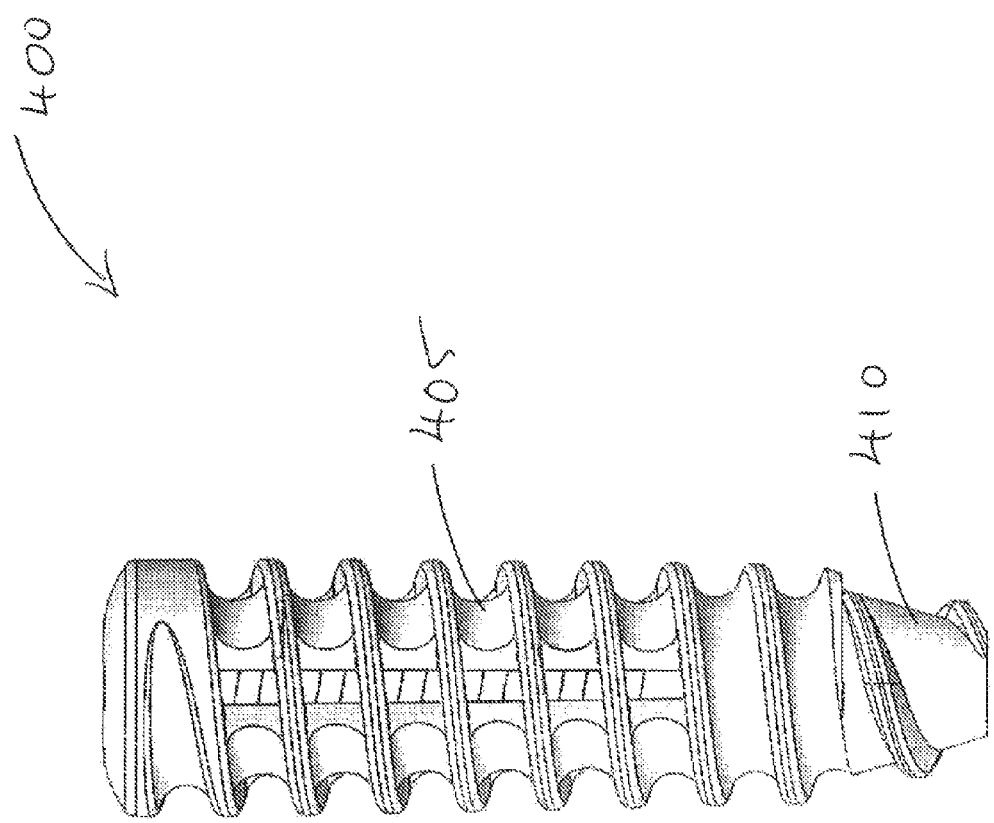

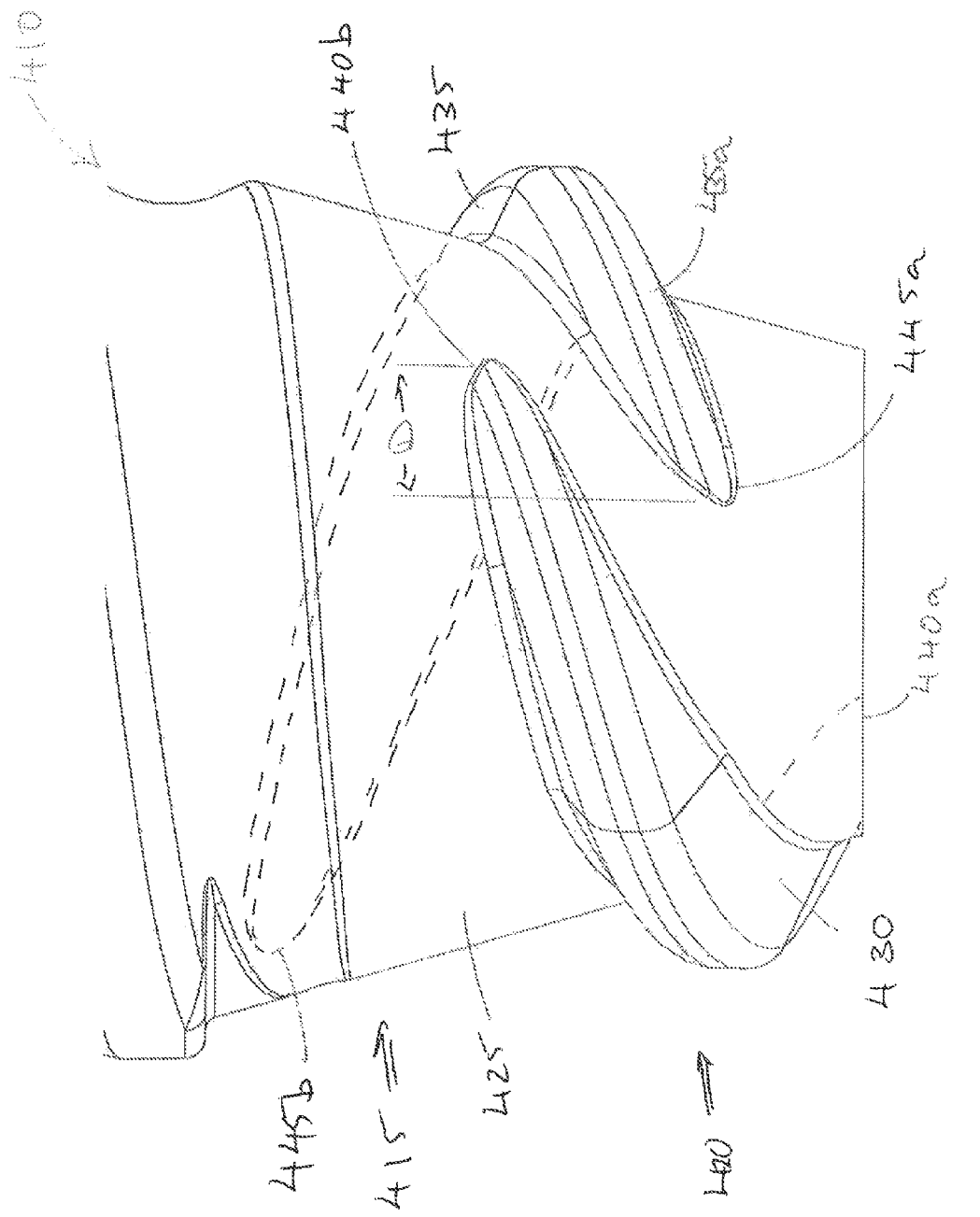

OPEN-ARCHITECTURE INTERFERENCE SCREW

CROSS-REFERENCE TO RELATED APPLICATION(S)

This application claims the benefit of U.S. Provisional Application No. 61/810,007, filed on Apr. 9, 2013, and entitled, "Open-architecture Interference Screw," the entirety of which is hereby incorporated by reference.

BACKGROUND

Interference screws have proven to be an effective means for securing tissue in a bone tunnel. However, the interference screw itself generally takes up a substantial amount of space within the bone tunnel, which can limit the surface area contact established between the tissue and the side wall of the bone tunnel. This in turn limits the region of bone-to-tissue in-growth, and hence can affect the strength of the repair. By way of example but not limitation, it has been estimated that the typical interference screw obstructs about 50% of the potential bone-to-tissue integration region.

SUMMARY

In one aspect, the present disclosure relates to an open-architecture interference screw for creating an interference fit between a bone tunnel and tissue. The interference screw includes a threaded body having a proximal end and a distal end, and a thread extending around the threaded body between the proximal end and distal end. The interference screw further includes a supporting spline extending along a cannulation through the threaded body between the proximal end and distal end. The supporting spline is engagable with a delivery device. The interference screw further includes at least one opening defined by an outer surface between the thread. The at least one opening is further defined by a ratio of open surface area to closed surface area. The ratio is selected such that, when torsionally loaded, the screw does not exhibit plastic deformation when inserted into an undersized bone tunnel. The interference screw further includes a tapered tip extending from the distal end of the threaded body. The tapered tip has a thread extending at least partway around the tapered tip.

In yet another aspect, the present disclosure relates to a delivery device and interference screw combination for creating an interference fit between a bone tunnel and tissue. The delivery device of the combination includes a handle and a shaft connected to the handle. The shaft includes a distal portion having a driving member. The interference screw includes a threaded body having a proximal end and a distal end, and a thread extending around the threaded body between the proximal end and distal end. The interference screw further includes a supporting spline extending along a cannulation through the threaded body between the proximal end and distal end. The supporting spline is engagable with a delivery device. The interference screw further includes at least one opening defined by an outer surface between the thread. The at least one opening is further defined by a ratio of open surface area to closed surface area. The ratio is selected such that, when torsionally loaded, the screw does not exhibit plastic deformation when inserted into an undersized bone tunnel. The interference screw further includes a tapered tip extending from the distal end of the threaded body. The tapered tip has a thread extending at least partway around the tapered tip. The interference screw is located on the distal portion of the delivery device such that the driving member engages the supporting spline of the interference screw.

In some examples, the interference screw may further include one or more of the following, alone or in any combination. The thread of the tapered tip may extend at least one full turn around the tapered tip. The thread of the tapered tip may also be a continuation of the thread of the threaded body. In other examples, the thread of the tapered tip is a partial thread extending less than one full turn around the tapered tip. Some of these examples include a first partial thread and a second partial thread, each extending a half turn around the tapered tip.

In some examples, the threaded body and tapered tip each have a different thread pitch. The thread pitch of the tapered tip may be between 1.5 and 3 times greater than the thread pitch of the threaded body.

In other examples, the threaded body has a constant diameter. The threaded body may have a wall thickness of 0.5-3.25 mm or a wall thickness that is a function of the diameter and length of the screw. The supporting spline may have a width of 1-2.5 mm. The thread of the threaded body may have a base width of 0.76-2.54 mm.

In some examples, the ratio of open surface area to closed surface area is a function of the diameter and length of the screw. In one example, in which the screw has a diameter of 11-12 mm and a length of 30-35 mm, the ratio is about one unit of open surface area to about three units of closed surface. In another example, in which the screw has a diameter of 7-10 mm and a length of 20-35 mm, the ratio is about one unit of open surface area to about four units of closed surface area. In yet another example, in which the screw has a diameter of 5-6 mm and a length of 20-25 mm, the ratio is about one unit of open surface area to about five units of closed surface area.

The at least one opening may be defined by a surface between adjacent proximal threads. Alternatively, the at least one opening may include at least one continuous opening between adjacent proximal threads and at least one discontinuous opening between adjacent distal threads. In this example, the at least one discontinuous opening has alternating segments of open surface area and closed surface area. In yet another example, the at least one opening is defined by a surface between alternating pairs of adjacent threads.

Other examples of the interface screw include a screw head comprising a surface extending from the threaded body into a hemispherical-like end portion.

Some examples of the interface screw are made from made from a combination of poly(lactic-co-glycolic) acid, β-Tricalcium phosphate, and calcium sulfate.

Further areas of applicability of the present disclosure will become apparent from the detailed description provided hereinafter. It should be understood that the detailed description and specific examples, while indicating the convenient example of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate examples of the present disclosure and together with the written description serve to explain the principles, characteristics, and features of the disclosure. In the drawings:

FIGS. 5A-D are views of another example of the open-architecture interference screw.

FIGS. 10A-B are side views of an example open-architecture interference screw having a tapered tip with two partial threads.

DETAILED DESCRIPTION OF THE EMBODIMENTS

The following description of the example is in no way intended to limit the disclosure, its application, or uses.

Figure 1A:
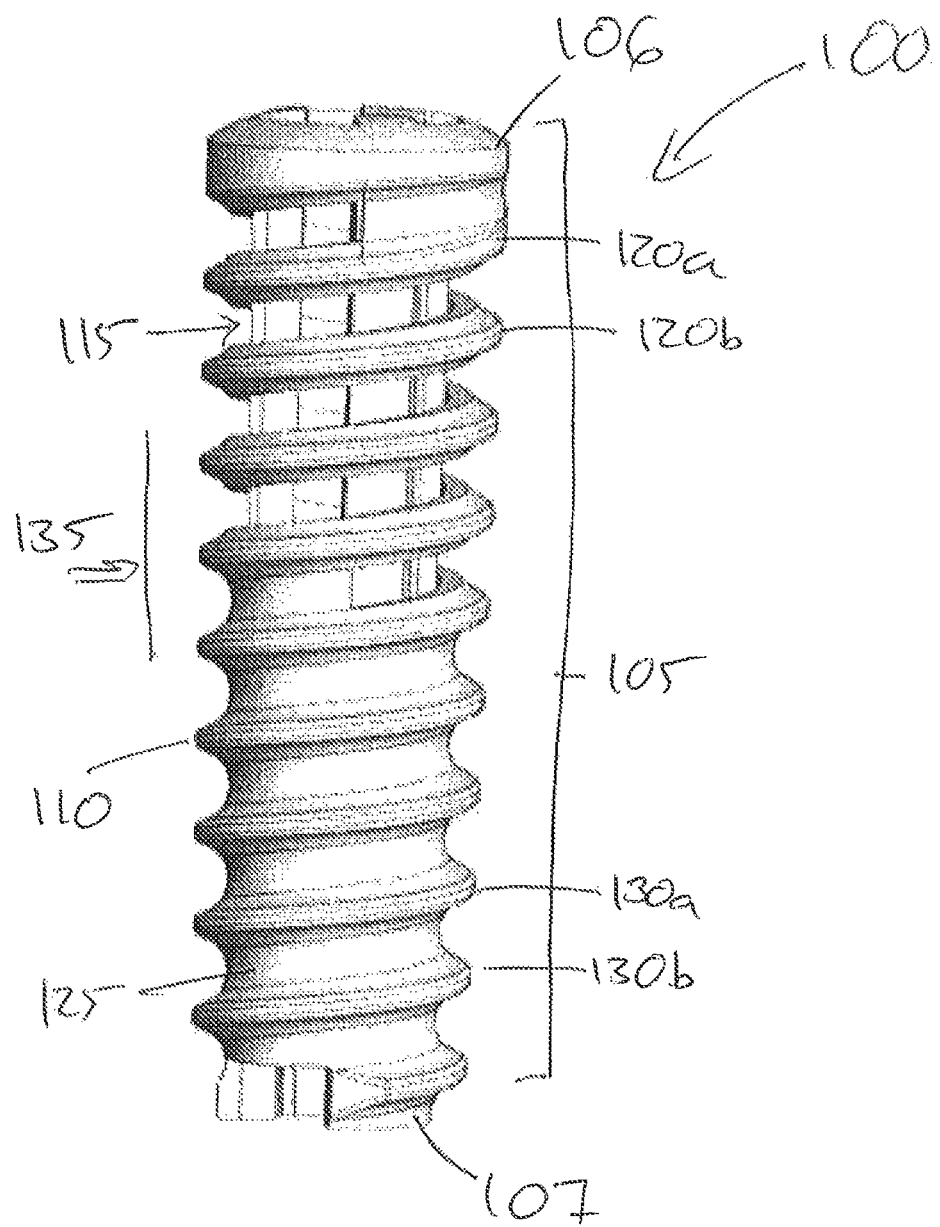
FIGS. 1A-B are views of an example of an open-architecture interference screw.
Figure 1B:
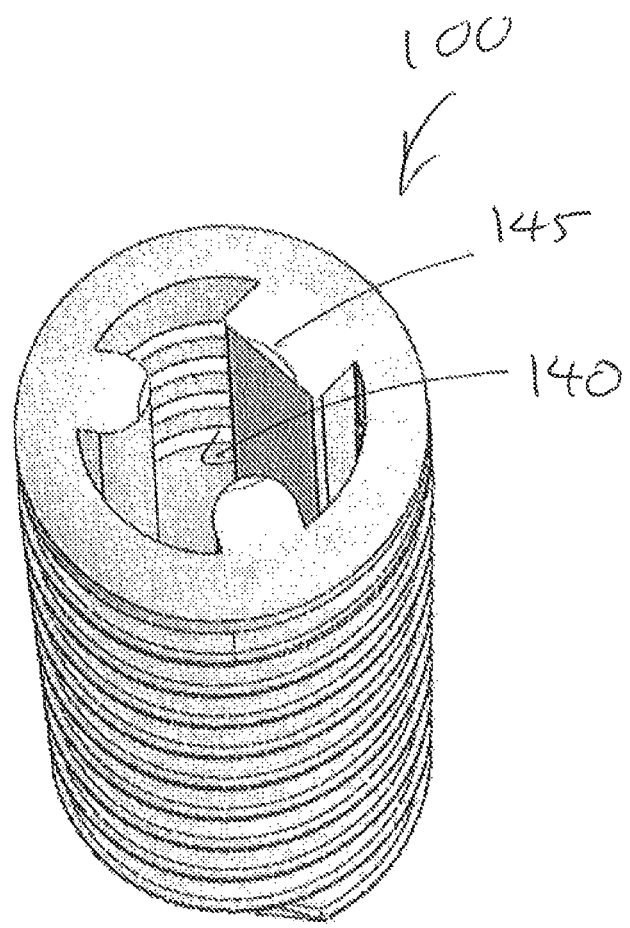

FIGS. 1A and 1B show an example of an interference screw 100. The interference screw 100 includes a threaded body 105 having a proximal end 106 and a distal end 107. A majority of the threaded body 105 includes screw threads 110 in the form of a helical coil, i.e. a connected series of continuous regularly spaced turns extending in a helical or spiral form substantially from the proximal end 106 to the distal end 107. The interference screw 100 further includes at least one opening 115 being defined by a surface between threads 110 of the threaded body 105. The opening 115 is further defined by a ratio of open surface area to closed surface area. It may convenient to refer to the ratio as a measure of degree of openness of an open architecture interference screw.

Having a ratio of open surface area to closed surface area is particularly advantageous, inasmuch as the ratio provides the structural strength (e.g., torsional, flexural, and/or compressive strengths) needed to set the interference screw 100 into position, and hold the tissue in position while bone-to-tissue in-growth occurs, while still providing extraordinary access through the threaded body 105 of the interference screw 100. Thus, cell and nutrient-bearing fluids can move substantially unimpeded through the threaded body 105 of interference screw 100, and tissue in-growth can occur across the threaded body 105 of interference screw 100.

A convenient example of the interference screw 100 has a ratio of open surface area to closed surface area that is a function of the diameter and length of the interference screw 100. For example, the ratio of open surface area to closed surface area increases as the length and/or diameter of the interference screw 100 increases. Described below in greater detail, a large-sized example of the interference screw 100, having a diameter of 11 mm-12 mm and a length of 30 mm-35 mm, has a ratio of about one unit of open surface area to about three units of closed surface area. A medium-sized example of the interference screw 100, having a diameter of 7 mm-10 mm and length of 20-35 mm, has a ratio of about one unit of open surface area to about four units of closed surface area. A small-sized example of the interference screw 100, having a diameter of 5-6 mm and a length of 20 mm-25 mm, has a ratio of about one unit of open surface area to about five units of closed surface area.

As best seen in FIG. 1A, there are openings 115 between adjacent proximal threads 120a,b of the interference screw 100. The interference screw 100 also includes closed surfaces 125 between adjacent distal threads 130a,b. As shown, the interference screw 100 is arranged with an open proximal portion and closed distal portion. This arrangement is advantageous because the closed surface 125 enhances the torsional strength, compressive strength and/or fexural strength (bend strength) of the distal portion of the interference screw 100. Increased structural strength is desirable at the distal end 107 of the interference screw 100 because it is prone to breaking as the interference screw 100 is inserted into an undersized pilot hole. The open proximal portion of the interference screw 100 advantageously promotes bone-to-tissue in-growth.

A convenient example of the interference screw 100 has a uniform taper 135. The threaded body 105 tapers from the proximal end 106 to the distal end 107. The taper 135 is advantageous to creating an interference fit between tissue and bone tunnel. When the interference screw 100 is inserted into the bone tunnel, the surface of the taper 135 fully contacts the tissue and drives it laterally into engagement with the opposing side wall of the bone tunnel. Greater contact between the interference screw 100 and tissue increases the pullout strength of the interference screw 100 and/or tissue.

The interference screw 100 further includes a cannulation 140 within the threaded body 105. The cannulation 140 extends longitudinally between the proximal end 106 and distal end 107 of the threaded body 105. In other words, the interference screw 100 may include an open helical coil defining an internal volume. The internal volume communicates with a region exterior to the open helical coil through the at least one opening 115 between the threads of the threaded body 105. There is a supporting spline 145 (three shown) extending longitudinally along the cannulation 140. The cannulation 140 and supporting spline 145 cooperatively engage a driver. The use of two or more supporting spline 145, rather than one supporting spline 145, may be advantageous because it may distribute the load imposed during rotation over a larger surface area.

Figure 2A:
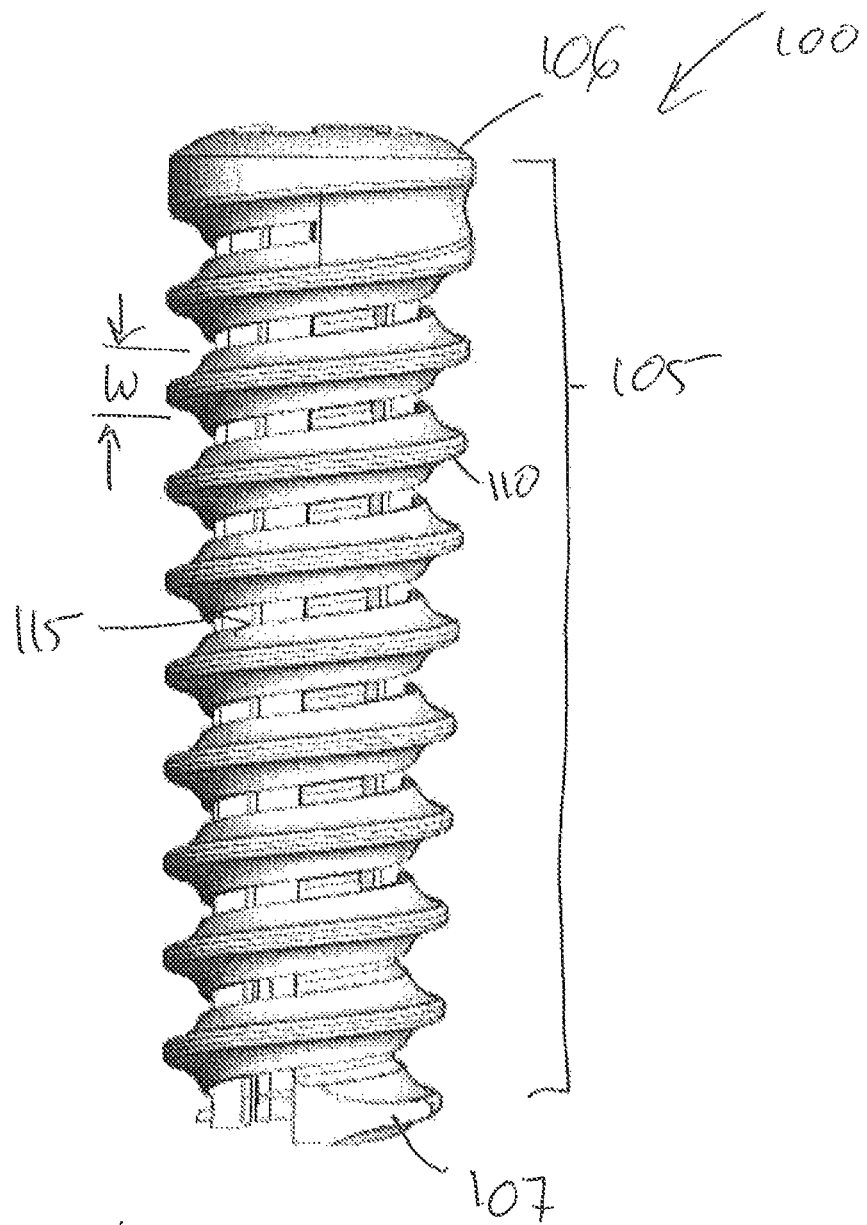
FIGS. 2A-B are views of another example of the open-architecture interference screw.
Figure 2B:
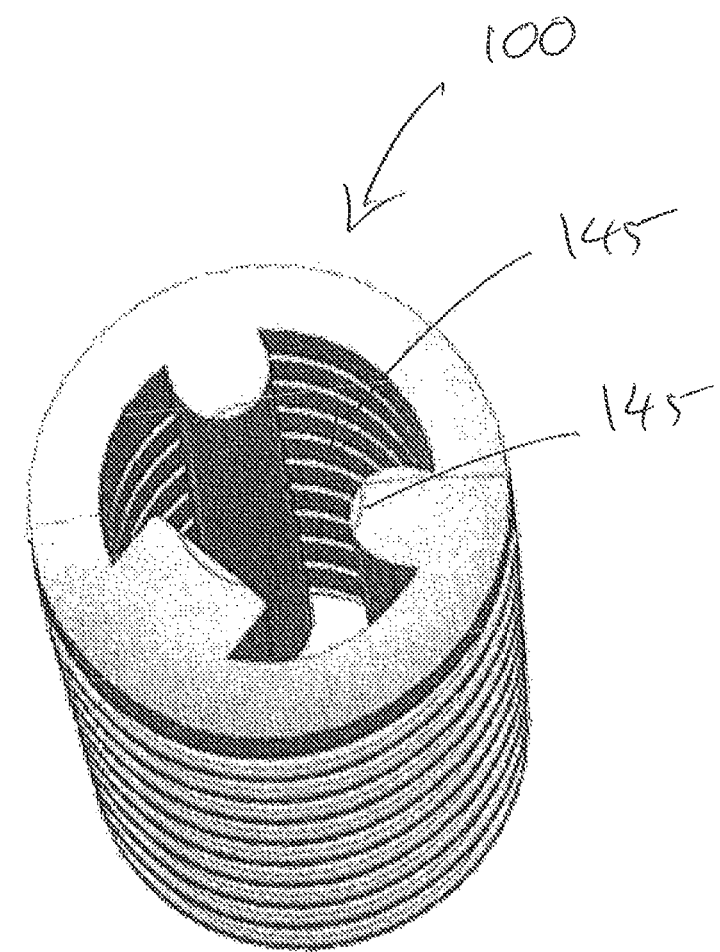

FIGS. 2A and 2B show another example of the interference screw 100. The interference screw 100 has threads 110 with a thread base width (W). In a convenient example, the thread base width is approximately 2.54 mm. One of the advantages of the interference screw 100 over other screws with thinner thread base widths is greater torsional strength and/or flexural strength.

Figure 3A:
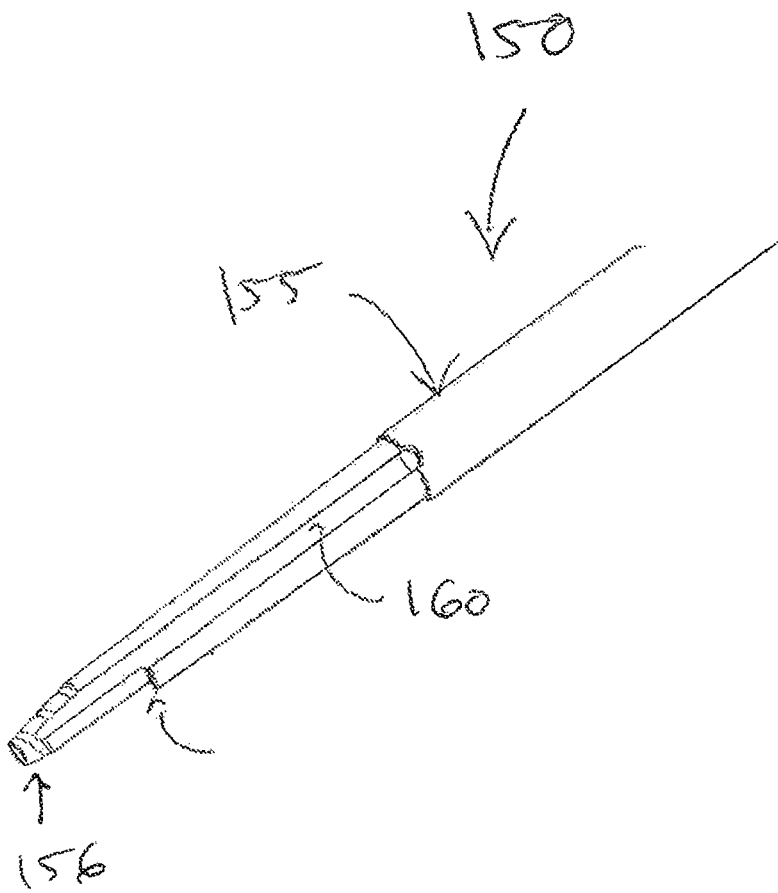
FIGS. 3A-C are views of an example combination of driver and open-architecture interference screw.
Figure 3B:
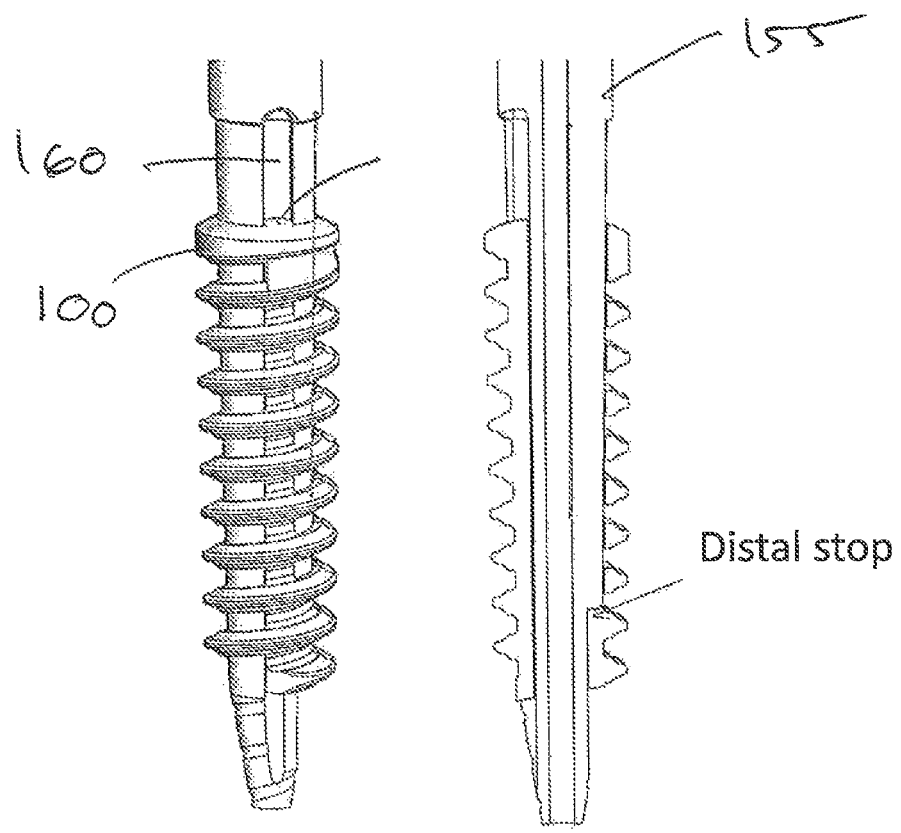

FIGS. 3A and 3B shows an example driver 150 used to insert the interference screw 100 into a bone tunnel (hole). The driver 150 includes a handle assembly (not shown) and a shaft 155 coupled to the handle assembly. The shaft 155 includes a distal end 156. The distal end 156 includes grooves (drive members) 160 and a distal stop 165. The grooves 160 extend a partial length of the shaft 155. The distal stop 165 is for use with a depth stop on the interference screw 100, which the driver 150 is used to implant into a bone tunnel during a tissue repair procedure, such as ligament reconstruction surgery.

Figure 3C:
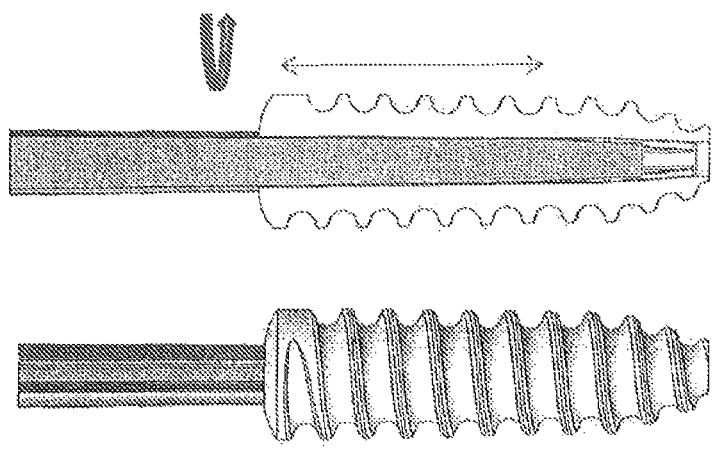

The distal end 156 of the shaft 155 is placed within the cannulation 140 of the interference screw 100 until the depth stop engages the distal stop 165 of the shaft 155. At this stopping point, the entire length of the interference screw 100 is fully supported by the driver 150. When the interference screw 100 is fully supported, the interference screw 100 is engaged by the driver 150, distributing the load across the entire length of the interference screw 100. FIG. 3C shows an example in which an interference screw is not fully supported, resulting in no torque applied to the tip of the interference screw, increasing the risk of screw breakage during insertion.

During insertion of the shaft 155 into the interference screw 100, the supporting splines 145 engage the grooves 160 and become housed within the grooves 160. A convenient example of the driver 150 includes a groove 160 for receiving substantially an entire length of the supporting spline 145. The interference screw 100 being mounted on the driver 150 such that the supporting spline 145 is substantially captured by the groove 160 of the driver 150. Rotating the driver 150 causes the interference screw 100 to rotate.

In example shown in FIGS. 3A and 3B, surface of the cannulation 140 and surface of the distal end 156 of driver 150 are tapered, expanding outwardly in the proximal direction, so that interference screw 100 and driver 150 form a positive seat. The surface of the cannulation 140 of the interference screw 100 is in direct contact with the tapered body diameter of the driver 150.

A convenient example of the driver 100 includes a tapered seat-forming thread (e.g., a tapered cutting thread, a tapered opening or dilating thread, etc.) formed in shaft distal to the grooves. Tapered seat-forming thread serves to precede interference screw into the space between the tissue and the wall of the bone tunnel, and then to form a lead-in or opening in the tissue and the wall of the bone tunnel for receiving the threads of threaded body, in much the same manner as a tap that creates a thread form.

During tissue (e.g., ligament) reconstruction surgery, for example, the end of the tissue (e.g., graft ligament) is placed in the bone tunnel and then the interference screw 100 is advanced into the bone tunnel via the use of driver 150 so that the interference screw 100 extends parallel to the bone tunnel and simultaneously engages both the tissue and the side wall of the bone tunnel. The interference screw 100 may be used in either the femoral or tibial tunnels, for example.

FIGS. 4A-D show an example of another interference screw 200. The interference screw 200 includes a threaded body 205 having a proximal end 206 and a distal end 207. The interference screw 200 further includes a tip 210 disposed at the distal end 207 of the threaded body 205. The tip 210 has a proximal end 211 and a distal end 212, and a taper 215. The tip 210 tapers from the proximal end 211 to the distal end 212. The tip 210 is advantageous to inserting the interference screw 200 into an undersized bone tunnel filled with a tissue graft. The distal end 212 of the tip 210 has a diameter smaller than the opening to the bone tunnel and, thus, allows compressive forces to be gradually placed upon both the bone tunnel and the tissue graft.

In one example of the interference screw 200, the threaded body 205 has a constant diameter. In another example of the interference screw 200, the threaded body 205 includes a taper different than the taper 215 of the tip 210. The threaded body 205 tapering from the proximal end to distal end (e.g., a 2 degree taper). The taper of the threaded body 205 is advantageous to creating an interference fit between tissue and bone tunnel. When the interference screw 200 is inserted into the bone tunnel, the surface of the taper fully contacts the tissue and drives it laterally into engagement with the opposing side wall of the bone tunnel. Greater contact between the interference screw 200 and tissue increases the pullout strength of the interference screw 200 and/or tissue. Because of the taper 215 of the tip 210, this example of the interference screw 200 is also easier to insert into a bone tunnel.

A majority of the threaded body 205 includes screw threads 220 in the form of a helical coil, i.e. a connected series of continuous regularly spaced turns extending in a helical or spiral form substantially from the proximal end 206 to the distal end 207. The interference screw 200 further includes at least one opening 225 being defined by a surface between the threads 220 of the threaded body 205. The opening 225 is further defined by a ratio of open surface area to closed surface area. This ratio is advantageous to promoting desirable bone-to-tissue in-growth through the opening 225. This ratio is also advantageous to providing structural strength (e.g., torsional and/or flexural), such that the interference screw 200 resists breaking when inserted into an undersized bone tunnel to create an interface fit between a bone tunnel and tissue. It may convenient to refer to the ratio as a measure of degree of openness of an open architecture interference screw.

A convenient example of the interference screw 200 has a ratio of open surface area to closed surface area that is a function of the diameter and length of the interference screw 200. For example, the ratio of open surface area to closed surface area increases as the length and/or diameter of the interference screw 200 increases. Described below in greater detail, a large-sized example of the interference screw 200, having a diameter of 11 mm-12 mm and a length of 30 mm-35 mm, has a ratio of about one unit of open surface area to about three units of closed surface area. A medium-sized example of the interference screw 200, having a diameter of 7 mm-10 mm and length of 20-35 mm, has a ratio of about one unit of open surface area to about four units of closed surface area. A small-sized example of the interference screw 200, having a diameter of 5-6 mm and a length of 20 mm-25 mm, has a ratio of about one unit of open surface area to about five units of closed surface area.

Figure 4A:
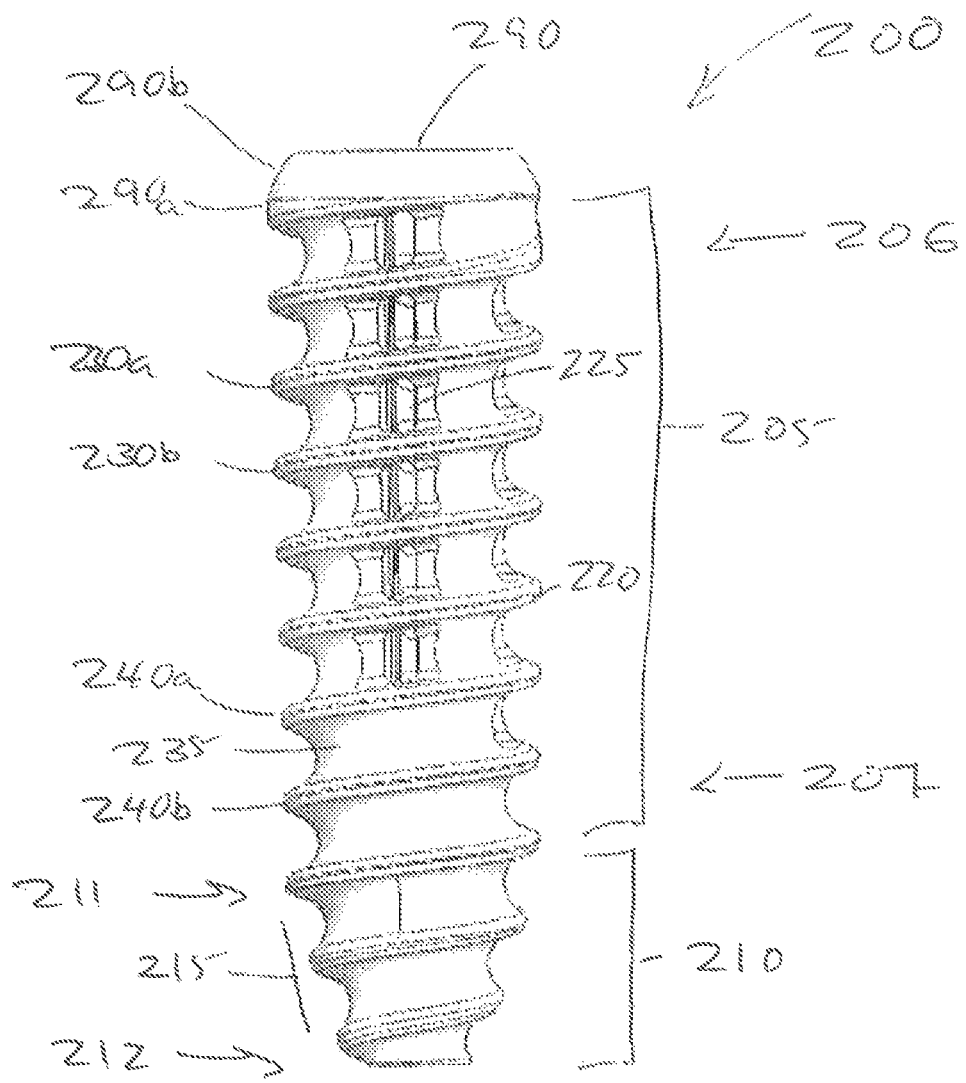
FIGS. 4A-C are views of an example of another open-architecture interference screw.
Figure 4B:
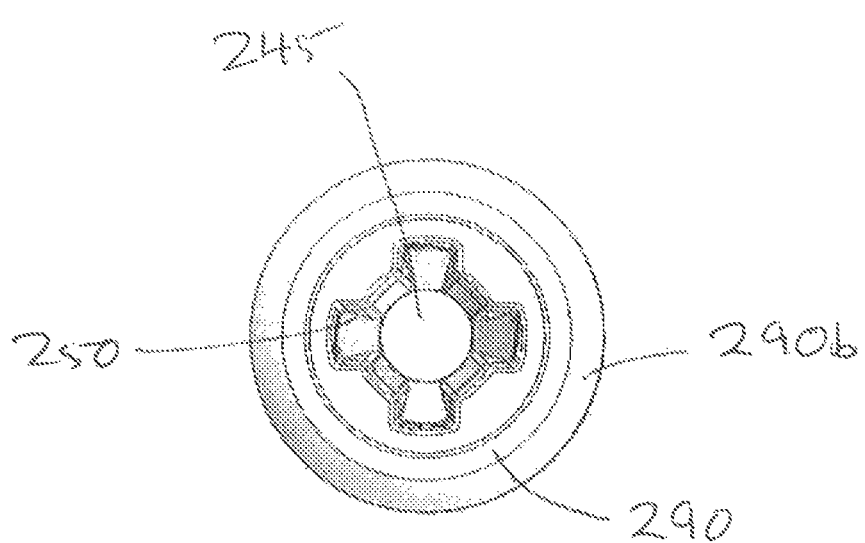
Figure 4C:
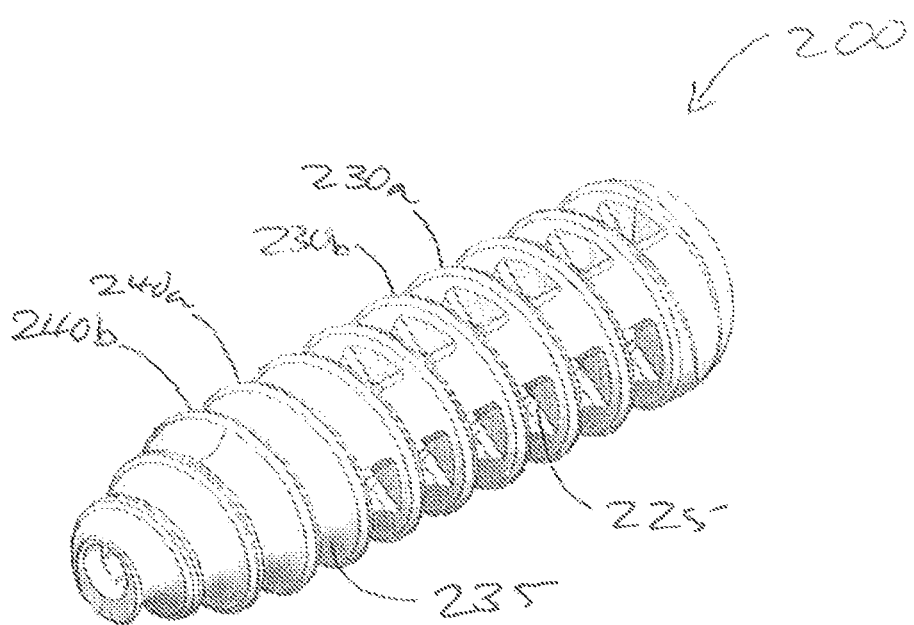
Figure 5A:
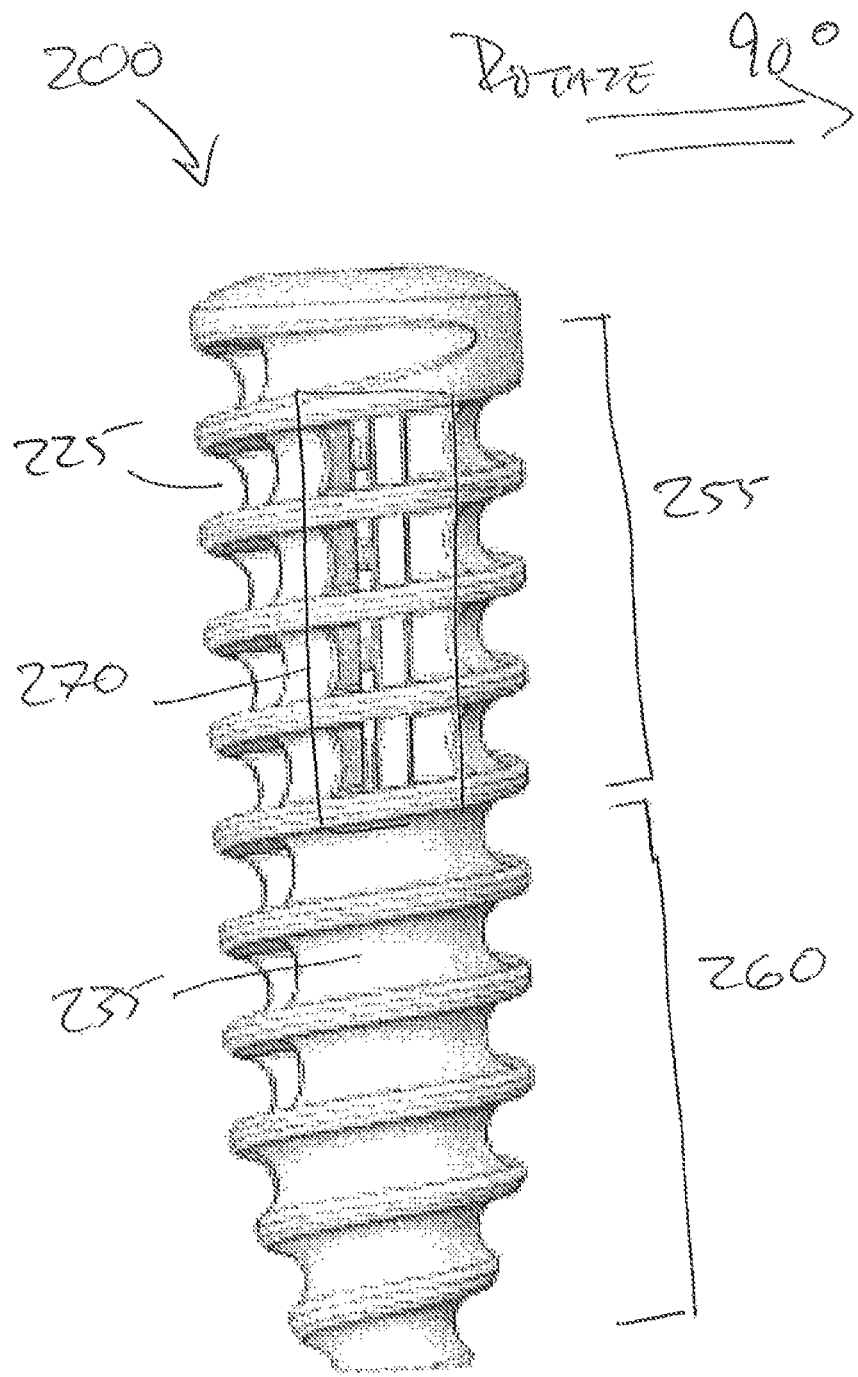
Figure 5B:
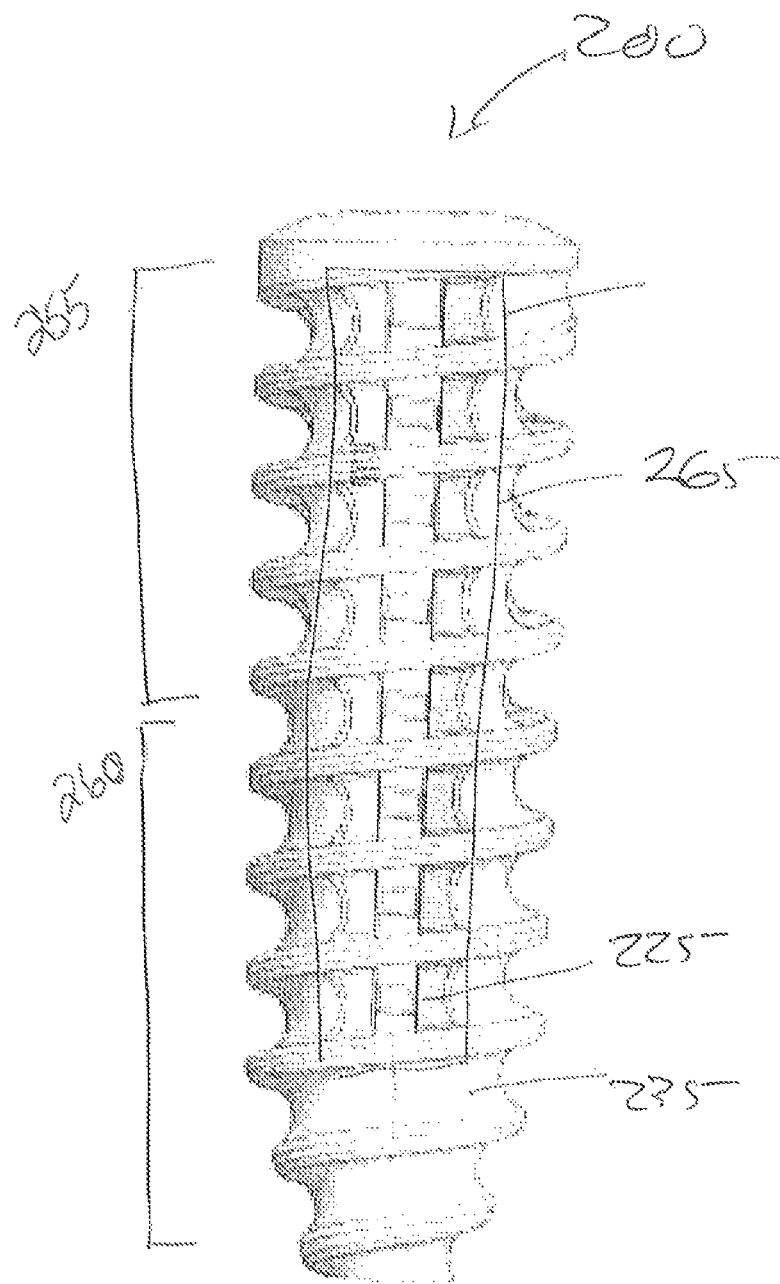
Figure 5C:
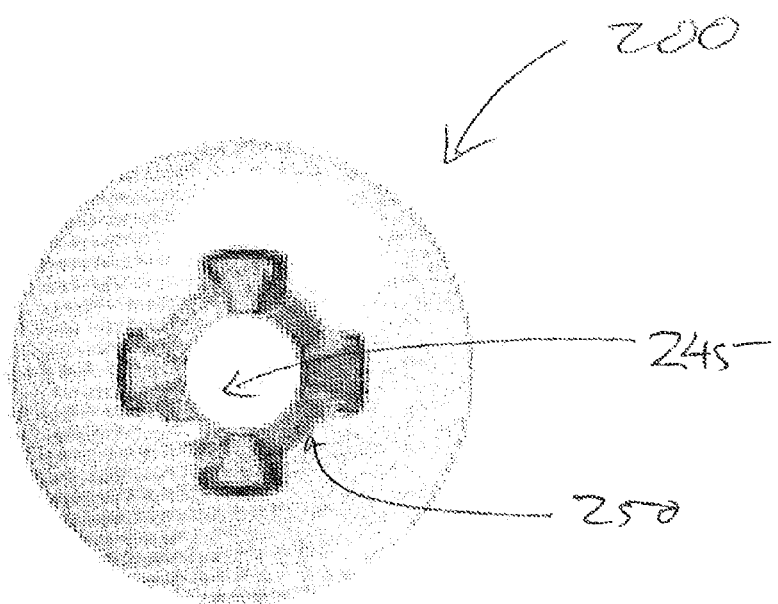

As best seen in FIG. 4A, there are openings 225 between adjacent proximal threads 230a,b of the interference screw 200. The interference screw 200 also includes closed surfaces 235 between adjacent distal threads 240a,b. As shown, the interference screw 200 is arranged with an open proximal portion and closed distal portion. This arrangement is advantageous because the closed surface enhances the torsional strength, compressive strength, and/or flexural strength of the distal portion 207 of the interference screw 200. Increased structural strength is desirable at the distal end of the interference screw 200 because it is prone to breaking as the interference screw 200 is inserted into an undersized bone tunnel. The open proximal portion of the interference screw 200 advantageously promotes bone-to-tissue in-growth.

The interference screw further includes a cannulation 245 within the threaded body 205. The cannulation 245 extends longitudinally between the proximal end 206 and distal end 207 of the threaded body 205. In other words, the interference screw 200 may include an open helical coil defining an internal volume. The internal volume communicates with a region exterior to the open helical coil through the at least one opening 225 between the threads 220 of the threaded body 205. There is a supporting spline 250 (four shown) extending longitudinally along the cannulation 245. The cannulation 245 and supporting spline 250 cooperatively engage a driver.

A convenient example of the interference screw 200 includes, at the proximal end 206, a screw head 290. The screw head 290 has a surface 290a that extends smoothly and continuously from the threaded body 205 into a hemispherical-like end portion 290b, as shown. In use, the screw head 290 rests against graft material and damage to graft fibers is possible. Beneficially, this arrangement of the surface 290a and hemispherical-like end portion 290b reduces the chance of such damage.

FIGS. 5A-D show another example of the interference screw 200. The interference screw 200 includes a proximal portion of continuous openings 255. The continuous openings 255 are defined by a surface between proximal threads 230a,b. The continuous openings 255 completely encircle the interference screw 200. The proximal portion of continuous openings 255 advantageously promotes bone-to-tissue in-growth.

The interference screw 200 further includes a distal portion of discontinuous openings 260. The discontinuous openings are defined by a surface between distal threads 240a,b. Along a path of the surface, the surface alternates openings 225 and closed surface areas 235. This alternating pattern of openings 225 and closed surface areas 235 improves the torsional and flexural strength of the distal portion of the interference screw 200 that advantageous to insert in the interference screw 200 into a bone tunnel.

In the example of the interference screw 200 shown, the openings 225 and closed surface areas 235 of the distal portion of discontinuous openings are arranged 90° to each other. For example, there is opening 225 and when the interference screw 200 is rotated 90°, there is a closed surface area 235. It may be convenient to call this arrangement of the openings 225 and closed surface areas 235 asymmetrical. Other arrangements are possible, for example the openings 225 and closed surface areas 235 are arranged at an angle less than 90° or greater than 90°. The interference screw 200 with asymmetrical arrangement of openings 225 and closed surface areas 235 has a tip strength greater than an interference screw with openings only. High tip strength is advantageous to inserting the interference screw 200 into a undersized bone tunnel.

The example of the interference screw 200 may be described as having a threaded body 205 with a number of sides (e.g., four). The first side of the threaded body 205 includes a first series of rectangular-shaped (or the regular shape) openings 265 extending from the proximal end 206 to the distal end 207 of the interference screw 200. (Best seen in FIG. 5B.) The first series of openings 265 has a first length. A second side of the threaded body 205 includes a second series of rectangular-shaped openings 270 extending from the proximal end 206 to the distal end 207 of the interference screw 200. (Best seen in FIG. 5A.) The second series 270 has a second length shorter than the first length. (Best seen in FIG. 5D.) The foregoing arrangement repeats on the remaining sides (i.e., long series of openings, short series of openings, long series of openings, short series of openings, etc.).

The result of the foregoing arrangement is a region near the distal end 207 of the interference screw 200 in which the openings 225 are between closed surface areas 235. The strength of the surrounding closed surface areas 235 compensate for the weakness caused by the openings 225 in the interference screw 200. This arrangement improves tip strength that is advantageous to inserting the interference screw 200 into a bone tunnel.

Figure 6A:
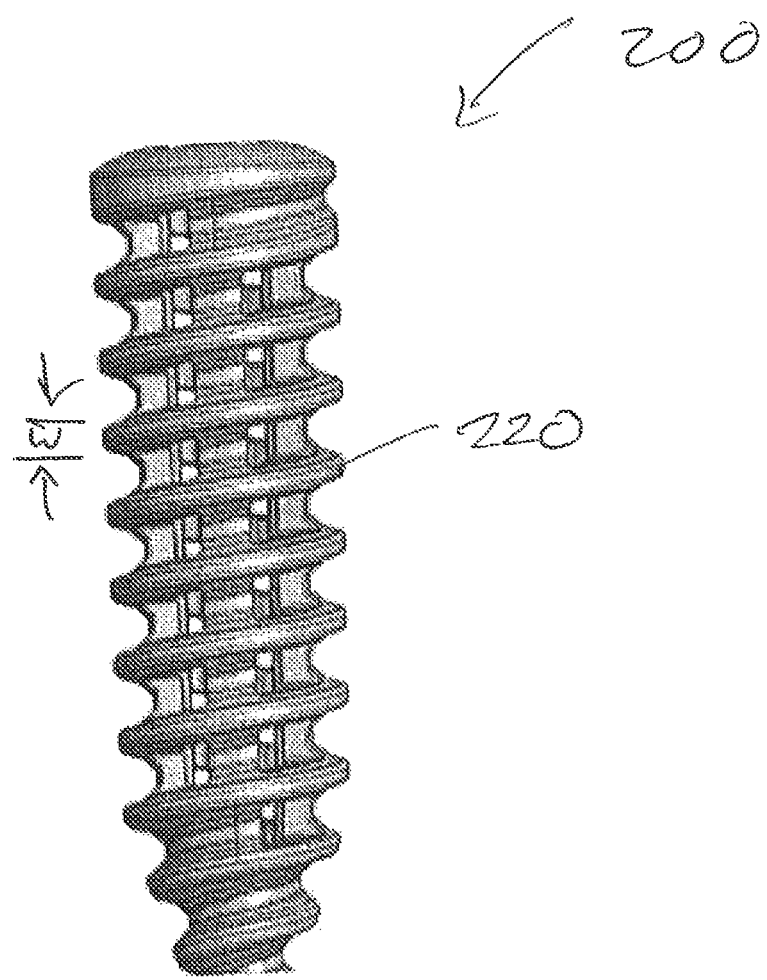
FIGS. 6A-C are views of another example of the open-architecture interference screw.
Figure 6B:
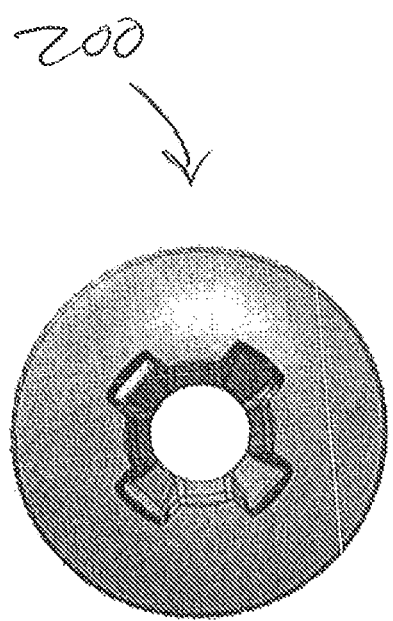
Figure 6C:
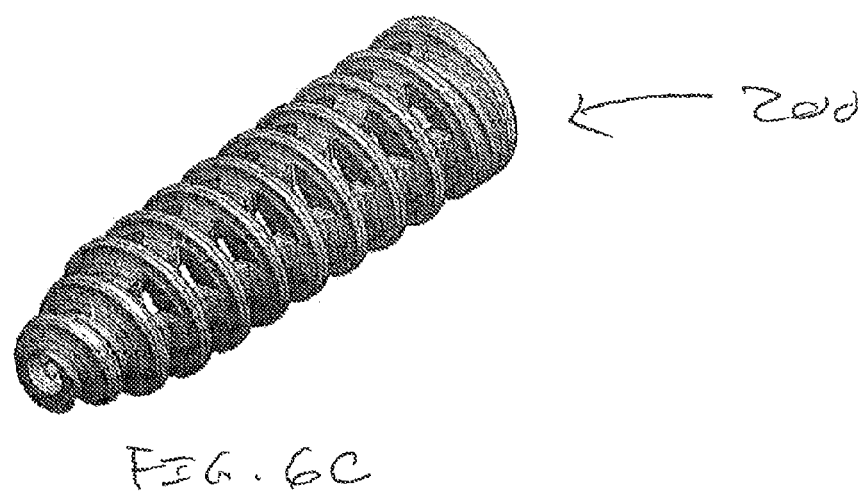

FIGS. 6A-C show another example of the interference screw 200. The interference screw 200 has threads 220 with a thread base width (W). In a convenient example, the thread base width is approximately 1.0 mm. One of the advantages of the interference screw 200 over other screws with thinner thread base widths is greater torsional strength and/or flexural strength.

Figure 7A:
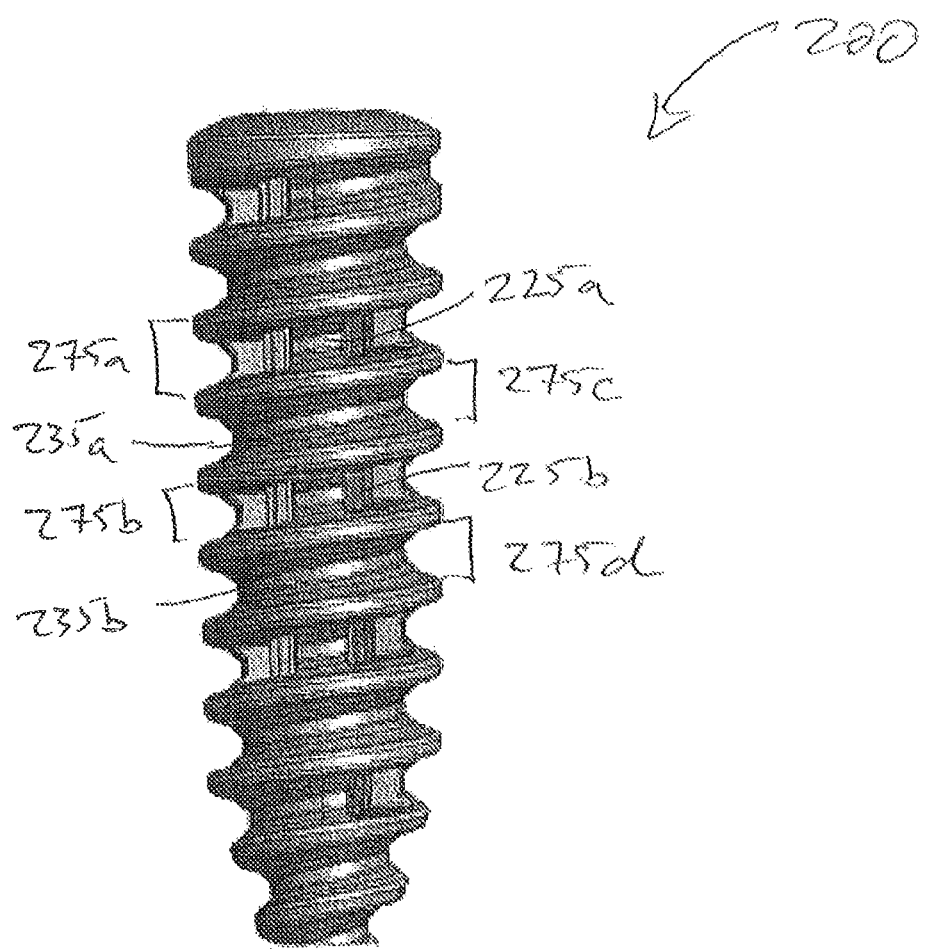
FIGS. 7A-C are views of another example of the open-architecture interference screw.
Figure 7B:
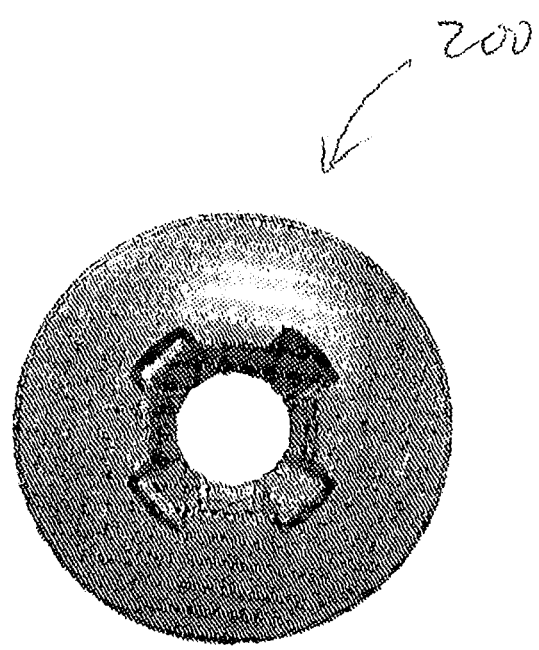
Figure 7C:
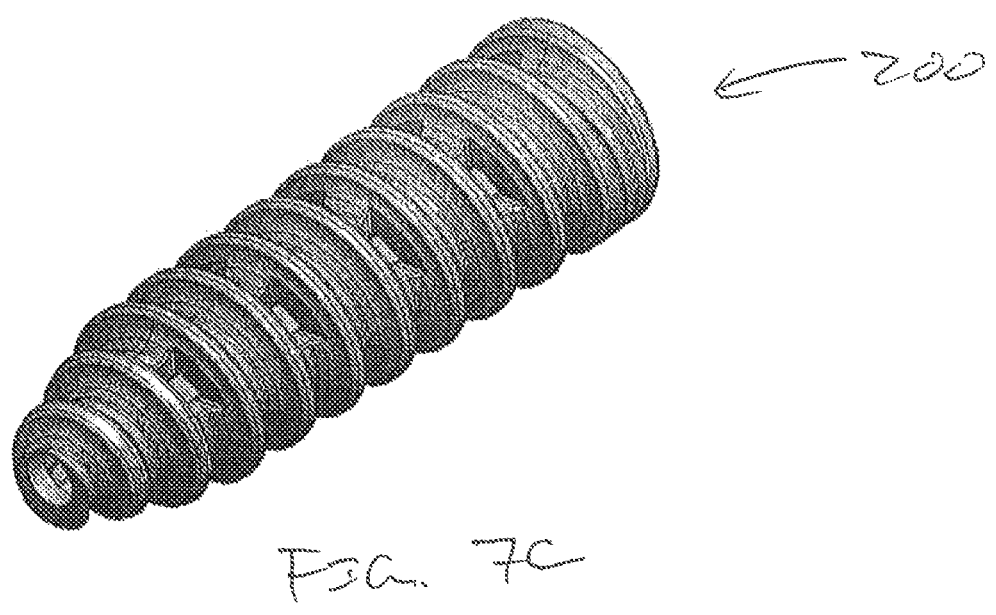

FIGS. 7A-C show another example of the interference screw 200. The interference screw 200 has an alternating pattern of openings 225 and closed surface areas 235. The alternating pattern extends over a length or substantially the entire length of the interference screw 200 (as shown). The openings 225 are between alternating pairs of adjacent threads 275. For example, the opening 225a is between a first pair of adjacent threads 275a and the opening 225b is between a second pair of adjacent threads 275b. The closed surface areas 235 are between alternating pairs of adjacent threads 275. For example, the closed surface areas 235a is between a third pair of adjacent threads 275c and the closed surface area 235b is between a fourth pair of adjacent threads 275d.

Figure 8P:
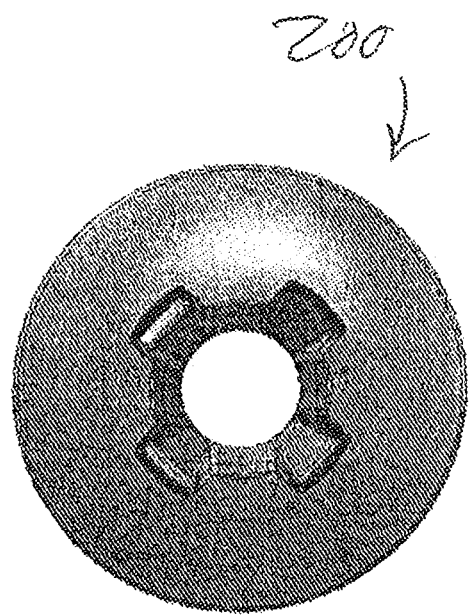
FIGS. 8A-C are views of another example of the open-architecture interference screw.

FIGS. 8A-C show another example of the interference screw 200. The interference screw 200 includes a proximal portion of uniform openings 280. The uniform opening 280 advantageously promote bone-to-tissue in-growth. The interference screw 200 further includes a distal portion of alternating pattern of openings and closed surface areas 285. (The alternating pattern is described above with reference to FIGS. 7A-C.) The alternating pattern of openings and closed advantageously increases tip strength.

Figure 9A:
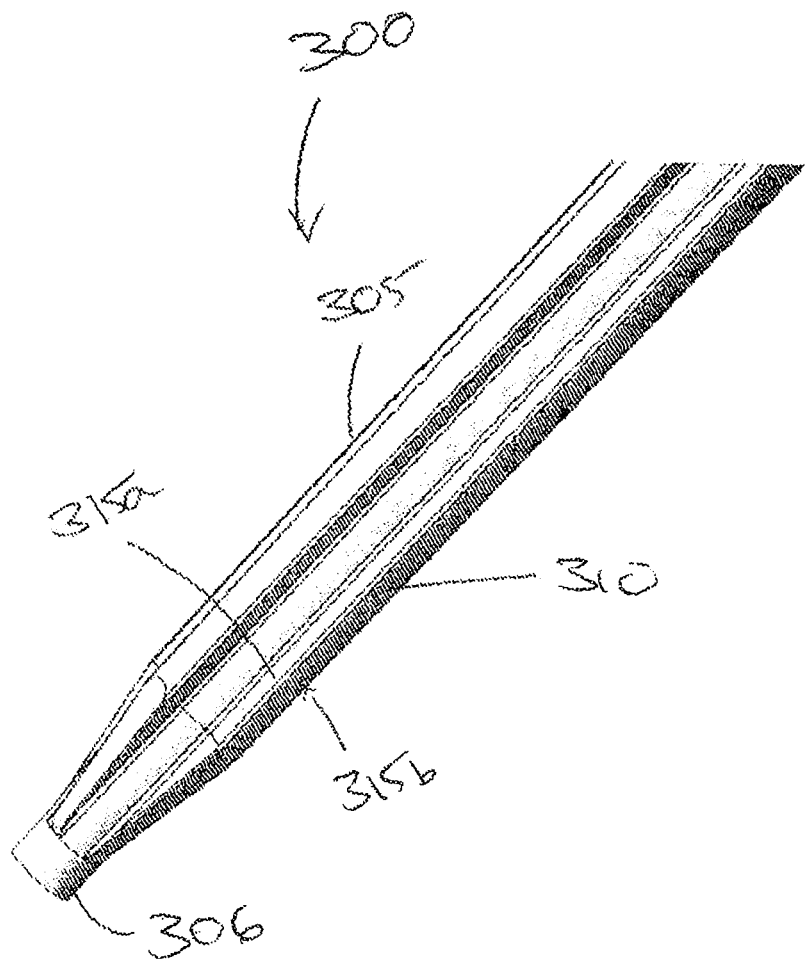
FIGS. 9A-B are views of an example combination of driver and open-architecture interference screw.
Figure 9P:
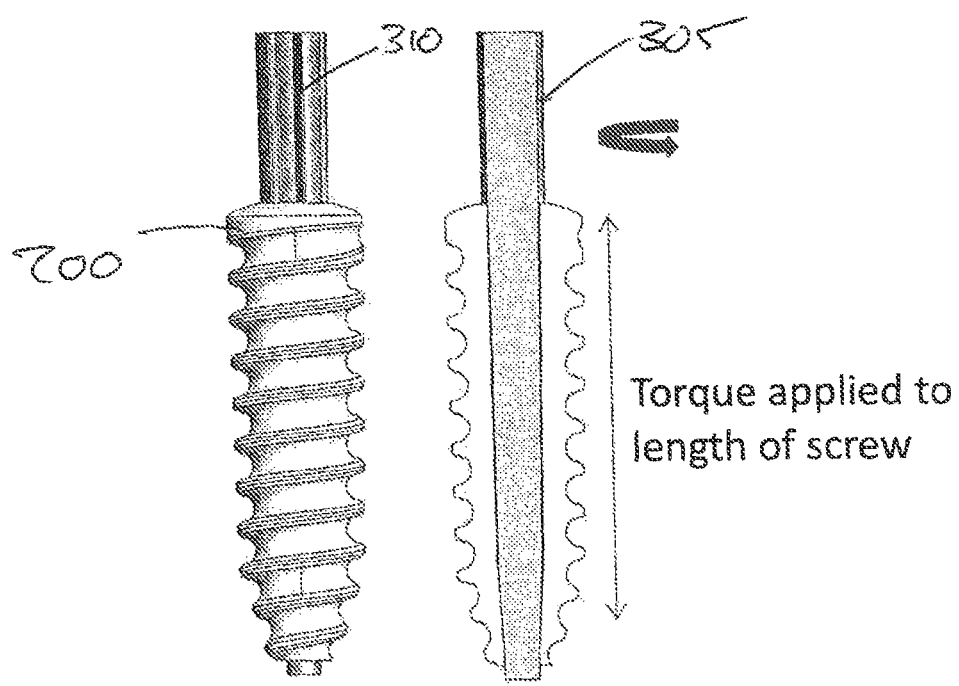

FIGS. 9A and 9B shows an example driver 300 used to insert the interference screw 200 into a bone tunnel (hole). The driver 300 includes a handle assembly (not shown) and a shaft 305 coupled to the handle assembly. The shaft includes a distal end 306 and a driving member 310 (four shown) extending from the distal end 306, and an opening for a guide wire used to position the screw during insertion (not shown). If desired, the drive member 310 extends a partial length of the shaft 305. The driving member 310 includes driving surfaces 315a,b for engaging the corresponding surfaces of the supporting spline 245.

The distal end 306 of the shaft 305 is placed within the cannulation 245 of the interference screw 200. When inserting the interference screw 200 into the bone tunnel, the entire length of the interference screw 200 is fully supported by the driver 300. This distributes the load across the entire length of the interference screw 200, reducing the risk of breakage during insertion.

In example shown in FIGS. 9A and 9B, surface of the cannulation 245 and surface of the distal end 306 of driver are tapered, expanding outwardly in the proximal direction, so that interference screw 200 and driver 300 form a positive seat. The surface of the cannulation 245 of the interference screw 200 is in direct contact with the tapered body diameter of the driver 300.

Figure 10C:
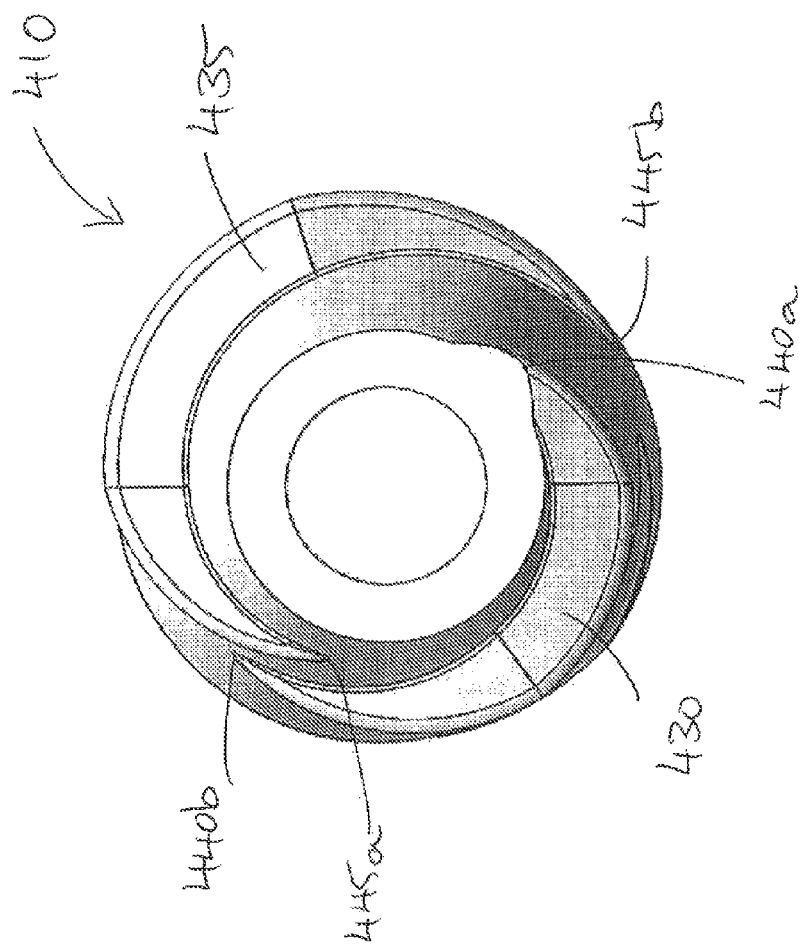
FIG. 10C-D are views of the tapered tip of FIGS. 10A-B with the body of the screw removed for clarity.
Figure 10D:
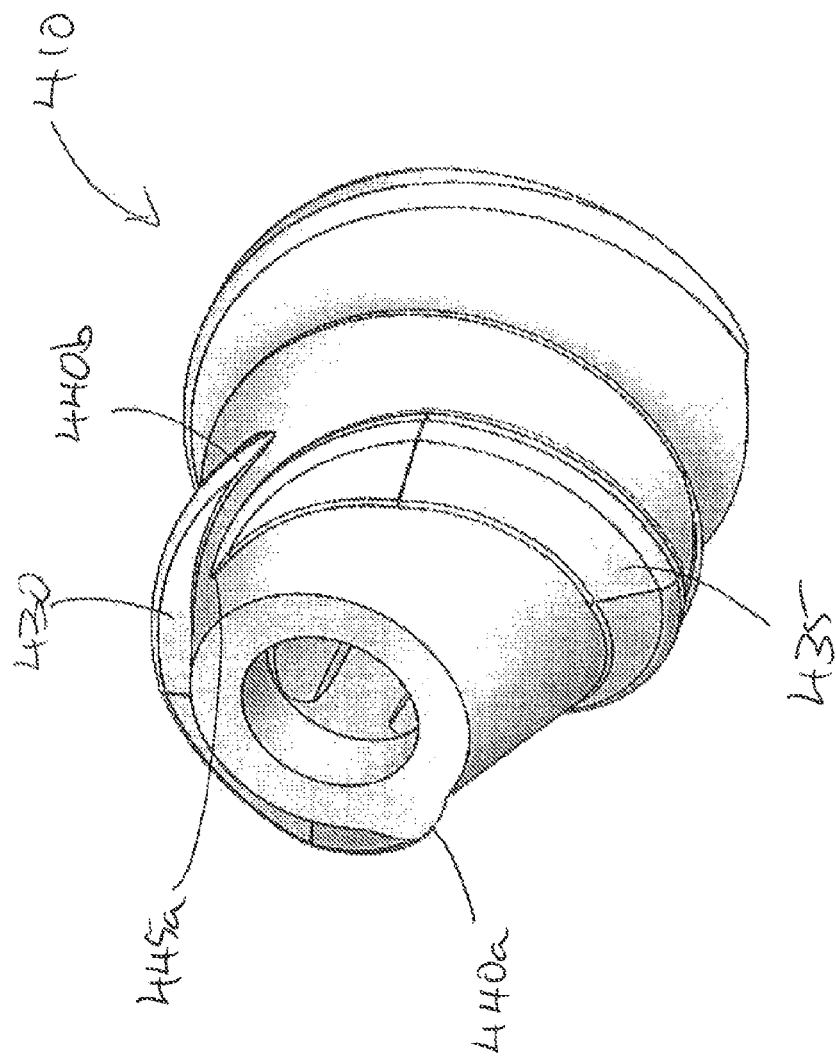

FIGS. 10A-D show an example of another interference screw 400. The interference screw 400 is similar to the interference screw 200 of FIGS. 4A-D with exception of the tip. The interference screw 400 includes a threaded body 405 and tapered tip 410 extending from the threaded body 405. With reference to FIG. 10B, the tapered tip 410 has a proximal region 415, distal region 420, and surface 425 extended between the proximal and distal regions 415, 420.

An example of the tapered tip 410 has a first partial thread 430 and second partial thread 435 extending partway or less than 360° around the tapered tip 410. The first and second threads 430, 435 each start and stop at different locations on the surface 425 of the tapered tip 410. In a convenient example of the tapered tip 410, the first partial thread 430 starts in the distal region 420 at point 440a and extends about 180° around the tapered tip 410 (best seen in FIGS. 10C and 10D with the threaded body 405 is removed for clarity) and stops at point 440b in the proximal region 415. The second partial thread 435 starts at point 445a distal to the stopping point 440b of the first partial thread 430. The second partial thread 435 extends about 180° around the tapered tip 410 (also best seen in FIGS. 10C and 10D) and stops at point 445b in the proximal region 415. The stopping point 440b of the first partial thread 430 and starting point 445a of the second partial thread 435 are spaced a distance D from one another. In other examples of the tapered tip 410, the first partial thread 430 and the second partial thread 435 are discontinuous or separate from one another.

In one example of the tapered tip 410, the partial threads 430, 435 taper towards the proximal region 415 with the same taper as the tapered tip 410. The minimum diameter of a given partial thread is at the distal terminus of the partial thread. The diameter of the partial thread increases to a maximum towards the proximal region 415 of the tapered tip 410. In a convenient example, the partial threads 430, 435 each have tapered ends, of which tapered ends 430a and 435a are shown in FIG. 10B. Each of the tapered ends has a height above the surface 425 of the tapered tip 410 and terminates at the same height as the surface 425. The smooth transition between the partial threads 430, 435 and the surface 425 of the tapered tip 410 advantageously minimizes damage to a graft from the interference screw 400.

Tracing an example of the partial thread with tapered ends, starting from the distal terminus of the partial thread, the diameter of the partial thread increases until a maximum is reached near the proximal region 415. Continuing to trace the partial thread past the maximum diameter, the diameter of the partial thread decreases until the proximal terminus of the partial thread is reached. In foregoing example, the partial thread extends about 180° around the tapered tip 410 but reaches a maximum diameter (and maximum root diameter) in less than 180°.

A convenient example of the tapered tip 410 has partial threads with a constant height and width. Another example of the tapered tip 410 has partial threads that are larger in the distal region 420 and decrease in size towards the proximal region 415. This arrangement provides an aggressive initial bite or purchase of surrounding tissue. Another example of the tapered tip 410 has partial threads that are smaller in the distal region 420 and increase in size towards the proximal region 415. This arrangement provides an initial bite less aggressive than the prior example.

In a convenient example of the tapered tip 410, the partial threads have a thread pitch greater than that of the threaded body 405. For example, the thread pitch of the partial threads on the tapered tip 410 is one-and-a-half to two times that of the threaded body 405. The larger thread pitch of the partial thread allows the tapered tip 410 to rapidly engage the surrounding tissue or bone tunnel.

Figure 11:
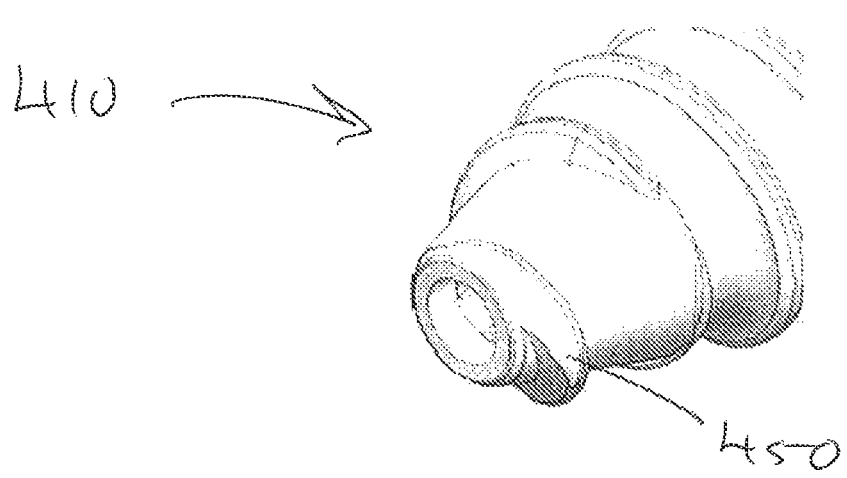
FIG. 11 is a view of an example tapered tip with one partial thread.

While the foregoing examples of the tapered tip 410 are described as having two partial threads, it should be apparent that any number of partial threads are possible, such as three or four. For example, FIG. 11 shows another example of the tapered tip 410 with one partial thread 450 extending partway or about 300° around the tapered tip 410.

In some examples of the interference screw 100, 200, 400 the threaded body 105, 205, 405 has a wall thickness of 0.5-3.25 mm. In other examples of the interference screw 100, 200, 400 the threaded body 105, 205, 405 has a wall thickness that is a function of the diameter and length of the screw.

In some examples of the interference screw 100, 200, 400 the supporting spline(s) 145, 250 has a width of 1-2.5 mm. Advantageously, a wide supporting spline distributes a torsional load better than a narrower supporting spline.

In some examples, the interference screw 100, 200, 400 may be completely or a portions thereof (e.g., the threaded body) made from a formulation of poly(lactic-co-glycolic) acid (PLGA), β-Tricalcium phosphate (β-TCP) and calcium sulfate, poly-L-lactic acid-hydroxyapatite (PLLA-HA), poly-D-lactide (PDLA), polyether ether ketone (PEEK) or variants thereof. Biocomposite examples of the interference screw 100, 200, 400 made from a combination of PLGA, β-TCP, and calcium sulfate are absorbable by the body, which is beneficial to natural healing. An example formulation of PLGA, β-TCP, and calcium sulfate is described in U.S. Pat. No. 8,545,866, the entirety of which is herein incorporated by reference. A copolymer of polyglycolic acid (PGA) and polytrimethylene carbonate (TMC) is another example of a bioabsorbable material. Other commonly used materials for implants are also contemplated by this disclosure. In any case, the interference screw 100, 200, 400 comprise a material that is capable of providing the strength needed to set the fixation device into position and to hold the tissue in position while bone-to-tissue in-growth occurs.

To examine the performance of the open-architecture interference screw, finite element analysis was used to simulate inserting the screw into an undersized bone tunnel with a delivery device. In the analysis, torque (torsional load) was applied to the inner portion of the screw that is in contact with the delivery device while the distal end of the screws was held in place. The torque at which the sample plastically deformed was recorded as the failure torque. The failure torque provides a measure of the torsional strength of a screw. The results of the analysis for a medium-size or 7 mm×25 mm (diameter by length) interference screw made from the formulation of PLGA, β-TCP, and calcium sulfate, described above, is provided below. (Similar results were found when the interference screw is made from PLLA-HA.)

| | Sample | Failure Torque (in * lb) | Open Area to Closed Area Ratio |
|---|---|---|---|
| 1 | Control (solid screw) | 18.26 | 0 to 1 |
| 2 | Sample 1 | 17.2 | 1 to 11 |
| 3 | Sample 2 | 15.23 | 1 to 11 |
| 4 | Sample 3 | 13.86 | 1 to 5 |
| 5 | Sample 4 | 16 | 1 to 4 |
| 7 | Sample 5 | 13.33 | 1 to 3 |
| 8 | Sample 6 | 5.59 | 1 to 2 |

A control with no openings (i.e., solid screw) had the highest failure torque (18.26 in*lb). From this baseline, samples of increasing degrees of openness were analyzed. In some samples, the degree of openness was attached with openings. In other samples, supporting splines or thread defining the openings were adjusted as well. It was observed that increasing the degree of openness decreased the failure torque.

Unexpectedly, increasing the degree of openness to one unit of open surface area to three units of closed surface area did not further decrease the torsional strength of the screw total but improved the torsional strength (increased from 13.86 to 16 in*lb). Increasing the degree of openness beyond this ratio, however, did not improve the performance but rather decreased performance (decreased from 16 to 13.33 in*lb). The results, therefore, demonstrate that for a medium-sized screw (e.g., 8 mm×25 mm), a ratio of about one unit of open surface area to about four units of closed surface area provides superior results. The results also demonstrated that, surprisingly, thickening the supporting splines provided better performance then thickening the threads of the screw.

Similar testing was performed with other sizes of screws. For a large-sized screw (e.g., 12 mm×25 mm), a ratio of about one unit of open surface area to about three units of closed surface area was determined to provide superior results. For a small-sized screw (e.g., 6 mm×20 mm), a ratio of about one unit of open surface area to about five units of closed surface area was determined to provide superior results. In some examples, increasing the wall thickness of the screw (e.g., when increasing the size of the screw), also increased the degree of openness.

For a large-sized screw (e.g., 12 mm×25 mm) made from PEEK, a ratio of about one unit of open surface area to about two units of closed surface area was determined to provide superior results. For a medium-sized screw (e.g., 8 mm×25 mm) made from PEEK, a ratio of about one unit of open surface area to about two units of closed surface area and a half was determined to provide superior results. For a small-sized screw (e.g., 6 mm×20 mm) made from PEEK, a ratio of about one unit of open surface area to about three and a half units of closed surface area was determined to provide superior results.

As various modifications could be made to the examples, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents. As used herein, the meaning of approximately, substantially, and about include their ordinary and customary meanings as well as being a certain percentage of a stated value e.g., 0.1%, 1%, and 10%.

What is claimed is:

1. An open-architecture interference screw for creating an interference fit between a bone tunnel and tissue, the screw comprising:
    a threaded body having a proximal end and a distal end, and a thread extending around the threaded body between the proximal end and distal end;
    at least one supporting spline extending along a cannulation through the threaded body between the proximal end and distal end, the at least one supporting spline engagable with a delivery device;
    at least one opening defined by an open surface between the thread, the at least one opening having a ratio of open surface area to closed surface area, the ratio being selected such that, when torsionally loaded, the screw does not exhibit plastic deformation when inserted into an undersized bone tunnel; and
    a tapered tip extending from the distal end of the threaded body, the tapered tip having a thread extending at least partway around the tapered tip;
    wherein a surface of the cannulation is tapered toward the distal end of the threaded body so as to form a positive seat with a corresponding tapered surface of the delivery device when the delivery device is engaged with the at least one supporting spline.

2. The open-architecture interference screw of claim 1 wherein the thread of the tapered tip extends at least one full turn around the tapered tip.

3. The open-architecture interference screw of claim 2 wherein the thread of the tapered tip is a continuation of the thread of the threaded body.

4. The open-architecture interference screw of claim 1 wherein the thread of the tapered tip is a partial thread extending less than one full turn around the tapered tip.

5. The open-architecture interference screw of claim 4 wherein the partial thread includes a first partial thread and a second partial thread, each extending a half turn around the tapered tip.

6. The open-architecture interference screw of claim 4 wherein the threaded body and tapered tip each have a different thread pitch.

7. The open-architecture interference screw of claim 6 wherein the thread pitch of the tapered tip is between 1.5 and 3 times greater than the thread pitch of the threaded body.

8. The open-architecture interference screw of claim 1 wherein the threaded body has a constant diameter.

9. The open-architecture interference screw of claim 1 wherein the threaded body has a wall thickness of 0.5-3.25 mm.

10. The open-architecture interference screw of claim 1 wherein the threaded body has a wall thickness that is a function of the diameter and length of the screw.

11. The open-architecture interference screw of claim 1 wherein the at least one supporting spline has a width of 1-2.5 mm.

12. The open-architecture interference screw of claim 1 wherein the thread has a base width of 0.76-2.54 mm.

13. The open-architecture interference screw of claim 1 wherein the ratio of open surface area to closed surface area is a function of the diameter and length of the screw.

14. The open-architecture interference screw of claim 1 wherein the screw has a diameter of 11-12 mm and a length of 30-35 mm; and wherein the ratio is about one unit of open surface area to about three units of closed surface area.

15. The open-architecture interference screw of claim 1 wherein the screw has a diameter of 7-10 mm and a length of 20-35 mm; and wherein the ratio is about one unit of open surface area to about four units of closed surface area.

16. The open-architecture interference screw of claim 1 wherein the screw has a diameter of 5-6 mm and a length of 20-25 mm; and wherein the ratio is about one unit of open surface area to about five units of closed surface area.

17. The open-architecture interference screw of claim 1 wherein the at least one opening is defined by the open surface between adjacent proximal threads.

18. The open-architecture interference screw of claim 1 wherein the at least one opening includes at least one continuous opening between adjacent proximal threads; and at least one discontinuous opening between adjacent distal threads, the at least one discontinuous opening having alternating segments of open surface area and closed surface area.

19. The open-architecture interference screw of claim 1 wherein the at least one opening is defined by the open surface between alternating pairs of adjacent threads.

20. The open-architecture interface screw of claim 1 wherein the threaded body further includes a screw head comprising a surface extending from the threaded body into a hemispherical-like end portion.

21. The open-architecture interface screw of claim 1 wherein the screw is made from a combination of poly (lactic-co-glycolic) acid, β-Tricalcium phosphate, and calcium sulfate.

22. A delivery device and open-architecture interference screw combination for creating an interference fit between a bone tunnel and tissue, the combination comprising:

a delivery device comprising a handle and a shaft connected to the handle, the shaft including a distal portion having a driving member, a surface of the distal portion being tapered;

an interference screw comprising:

a threaded body having a proximal end and a distal end, and a thread extending around the threaded body between the proximal end and distal end;

at least one supporting spline extending along a cannulation through the threaded body between the proximal end and distal end, the supporting spline engagable with a delivery device;

at least one opening defined by an open surface between the thread, the at least one opening having a ratio of open surface area to closed surface area, the ratio being selected such that, when torsionally loaded, the screw does not exhibit plastic deformation when inserted into an undersized bone tunnel; and a tapered tip extending from the distal end of the threaded body, the tapered tip having a thread extending at least partway around the tapered tip;

wherein the interference screw is located on the distal portion of the delivery device such that the driving member engages the at least one supporting spline of the interference screw; and wherein a surface of the cannulation is tapered toward the distal end of the threaded body so as to form a positive seat with the tapered surface of the distal portion of the delivery device when the delivery device is engaged with the at least one supporting spline.

\* \* \* \* \*